United States Patent [19]
Blaschke et al.

[11] Patent Number: 6,004,948
[45] Date of Patent: Dec. 21, 1999

[54] DERIVATIVES OF BENZOSULPHONAMIDES AS INHIBITORS OF THE ENZYME CYCLOOXYGENASE II

[75] Inventors: Heinz Blaschke, Linz; Peter Kremminger, Asten; Michael Hartmann, Linz; Harald Fellier, Linz; Jörg Berg, Linz, all of Austria; Thomas Christoph, Aachen, Germany; Franz Rovenszky; Dagmar Stimmeder, both of Linz, Austria

[73] Assignee: Nycomed Austria GmbH, Austria

[21] Appl. No.: 09/000,049

[22] PCT Filed: Jul. 5, 1996

[86] PCT No.: PCT/EP96/02954

§ 371 Date: Sep. 3, 1998

§ 102(e) Date: Sep. 3, 1998

[87] PCT Pub. No.: WO97/03953

PCT Pub. Date: Feb. 6, 1997

[30] Foreign Application Priority Data

Jul. 21, 1995 [AT] Austria ..................... 1242/95
Jul. 21, 1995 [AT] Austria ..................... 1243/95

[51] Int. Cl.$^6$ .................................................. A61K 31/18
[52] U.S. Cl. .......................... 514/155; 514/156; 514/158; 514/211; 514/222.8; 514/605; 564/97; 564/99; 540/544; 540/546; 548/136; 548/300.1; 548/207; 546/301; 546/329; 546/300; 549/66; 549/73; 549/72
[58] Field of Search .................. 564/97, 99; 540/544, 540/546; 544/106; 546/300, 301, 329; 548/136, 300.1, 325.1, 207; 549/66, 72, 73; 514/155, 156, 158, 211, 222.8, 605

[56] References Cited

U.S. PATENT DOCUMENTS 3,139,381  6/1964  Novello .
3,288,852  11/1966  Dunbar .
3,560,512  2/1971  Skorcz .
3,755,605  8/1973  Moore .
3,906,024  9/1975  Moore .
4,064,239  12/1977  Mrozik .
4,518,594  5/1985  Kasamati .
4,874,846  10/1989  Chene .
5,374,764  12/1994  Yoshikawa .

FOREIGN PATENT DOCUMENTS

WO94/13635  6/1994  WIPO .

*Primary Examiner*—Paul J. Killos
*Assistant Examiner*—Jean F Vollano
*Attorney, Agent, or Firm*—Weneroth, Lind & Ponack, L.L.P.

[57] ABSTRACT

Compounds of the formula (I) in which A is oxygen, sulphur or NH; B is a group of the formula (IIa) or (IIb); and the other variables have the meaning given in claim 1, may be used as inhibitors of the enzyme cyclooxygenase II

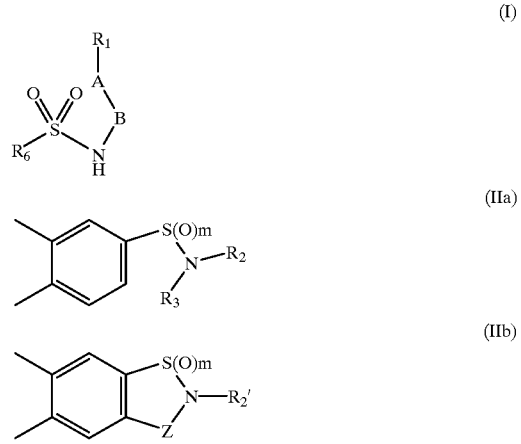

7 Claims, No Drawings

DERIVATIVES OF BENZOSULPHONAMIDES AS INHIBITORS OF THE ENZYME CYCLOOXYGENASE II

This is the national phase of PCT/EP96/02954 filed Jul. 5, 1996 now WO97/03953.

The invention relates to new derivatives of benzenesulphonic acids having anti-inflammatory activity.

Prostaglandins play a crucial part in inflammatory processes and the inhibition of prostaglandin formation, particularly the formation of $PGG_2$, $PGH_2$ and $PGE_2$ is the property common to anti-inflammatory compounds. The known non-steroidal anti-inflammatory drugs (NSAIDs) which reduce prostaglandin-induced pain and swelling in inflammatory processes also influence prostaglandin-regulated processes which do not accompany inflammatory processes. Therefore, the majority of known NSAIDs cause undesirable side effects at higher doses, sometimes even life-threatening ulcers, particularly gastric ulcers, gastric bleeds and the like. This seriously restricts the therapeutic potential of these compounds.

Most known NSAIDs inhibit the formation of prostaglandins by inhibiting enzymes in human arachidonic acid metabolism, particularly by inhibiting the enzyme cyclooxygenase (COX). An enzyme of human arachidonic metabolism which has only recently been discovered is the enzyme cyclooxygenase II (COX-2). (Proc. Natl. Acad. Sci. USA, 89, 7384, 1992). COX-2 is induced by cytokines or endotoxins. The discovery of this inducible enzyme which plays a decisive role in inflammatory processes opens up the possibility of searching for selectively acting compounds with an anti-inflammatory effect which will inhibit the inflammatory process more effectively without influencing other prostaglandin-regulated processes and at the same time having fewer and less severe side effects.

From WO 94/13635, 5-methylsulphonamide-1-indanones are known which inhibit the enzyme cyclooxygenase II and can therefore be used for the treatment of inflammatory processes. The potential and side effects of these compounds have not yet been fully investigated. Moreover, these known compounds have poor solubility and therefore have significant disadvantages in formulation and use. Therefore, there is still a need for new cyclooxygenase II-selective compounds which are safe in terms of their activity and side effects profile and are effective in use in the treatment of inflammatory processes.

The aim of the present invention was therefore to prepare new non-steroidal anti-inflammatory drugs (NSAIDs) which selectively inhibit cyclooxygenase II (COX-2) and therefore have less and less severe undesirable side effects.

This aim was unexpectedly achieved by preparing new derivatives of benzenesulphonic acids. These new compounds, by virtue of their selective effect on the enzyme cyclooxygenase II, have excellent anti-inflammatory, analgesic, anti-pyretic and anti-allergic properties without having the extremely undesirable side effects of the known anti-inflammatories.

The present invention therefore relates to compounds of formula I

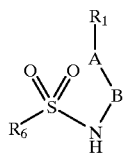

I wherein

A denotes oxygen, sulphur or NH, $R_1$ denotes a cycloalkyl, aryl or heteroaryl group optionally mono- or polysubstituted by halogen, alkyl, $CF_3$ or alkoxy B denotes a group of formula IIa or IIb

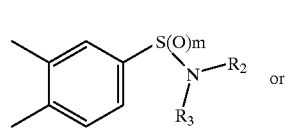

IIa or

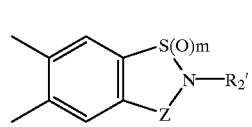

IIb $R_2$ and $R_3$ independently of each other denote hydrogen, an optionally polyfluorinated alkyl radical, an aralkyl, aryl or heteroaryl radical or a radical $(CH_2)_n$—X, or $R_2$ and $R_3$ together with the N-atom denote a three- to seven-membered, saturated, partially or totally unsaturated heterocycle with one or more heteroatoms N, O or S, which may optionally be substituted by oxo, an alkyl, alkylaryl or aryl group or a group $(CH_2)_n$—X, $R_2'$ denotes hydrogen, an optionally polyfluorinated alkyl group, an aralkyl, aryl or heteroaryl group or a group $(CH_2)_n$—X, wherein X denotes halogen, $NO_2$, —$OR_4$, —$COR_4$, —$CO_2R_4$, —$OCO_2R_4$, —CN, —$CONR_4OR_5$, —$CONR_4R_5$, —$SR_4$, —$S(O)R_4$, —$S(O)_2R_4$, —$NR_4R_5$, —NHC(O)$R_4$, —$NHS(O)_2R_4$ Z denotes —$CH_2$—, —$CH_2$—$CH_2$—, —$CH_2$—$CH_2$—$CH_2$—, —$CH_2$—CH═CH—, —CH═CH—$CH_2$—, —$CH_2$—CO—, —CO—$CH_2$—, —NHCO—, —CONH—, —$NHCH_2$—, —$CH_2NH$—, —N═CH—, —NHCH—, —$CH_2$—$CH_2$—NH—, —CH═CH—, >N—$R_3$, >C═O, >S(O)$_m$, $R_4$ and $R_5$ independently of each other denote hydrogen, alkyl, aralkyl or aryl, n is an integer from 0 to 6, $R_6$ is a straight-chained or branched $C_{1-4}$-alkyl group which may optionally be mono- or polysubstituted by halogen or alkoxy, or $R_6$ denotes $CF_3$, and m denotes an integer from 0 to 2, with the proviso that A does not represent O if $R_6$ denotes $CF_3$, and the pharmaceutically acceptable salts thereof.

A denotes oxygen, sulphur or NH.

$R_1$ denotes a cycloalkyl group, e.g. a cyclohexyl or cyclopentyl group, an aryl group, such as a phenyl group, or a heteroaryl group, e.g. a furyl, thienyl, thiazolyl, imidazolyl, thiadiazolyl, pyridyl or pyrazolyl group.

These groups may optionally be mono- or polysubstituted by halogen, such as Cl, F or Br or by $CF_3$ or $C_{1-4}$-alkyl, such as methyl, ethyl, propyl, isopropyl, butyl, isobutyl or tert.-butyl or $C_{1-4}$-alkoxy, such as methoxy, ethoxy, propoxy or butoxy.

$R_2$ and $R_3$ independently of each other denote hydrogen, an optionally polyfluorinated $C_{1-6}$-alkyl group, such as methyl, an ethyl, a propyl, an isopropyl, a butyl, an isobutyl, a tert.-butyl, a pentyl, an isopentyl, a hexyl or an isohexyl group, a group $CF_3$ or $C_2F_5$, an aralkyl group having 1 to 4 carbon atoms in the alkyl chain, such as a benzyl group, an ethylphenyl group, an aryl group, e.g. a phenyl group, or a heteroaryl group, e.g. a pyridyl group, a pyridazinyl group, a thienyl group, a thiazolyl group or an isothiazolyl group.

$R_2$ and $R_3$ may also independently of each other denote a group $-(CH_2)_n-X$, wherein X denotes halogen, $-NO_2$, $-OR_4$, $-COR_4$, $-CO_2R_4$, $-OCO_2R_4$, $-CN$, $-CONR_4OR_5$, $-CONR_4R_5$, $-SR_4$, $-S(O)R_4$, $-S(O)_2R_4$, $-NR_4R_5$, $-NHC(O)R_4$, $-NHS(O)_2R_4$, and n is an integer from 0 to 6. Examples of such groups are haloalkyl groups, such as chloromethyl, chloroethyl, the group $-CN$, nitroalkyl groups, such as nitromethyl, nitroethyl, or cyanoalkyl groups, such as cyanomethyl, cyanopropyl, cyanohexyl, a hydroxy group or hydroxyalkyl groups such as hydroxymethyl, hydroxyethyl, hydroxypropyl or bis-hydroxymethyl-methyl. Other examples are alkoxy groups such as methoxy, ethoxy, propoxy, butoxy, pentoxy, the groups methyloxy-ethyl, ethyloxy-methyl, carboxylic acid groups such as ethoxycarbonyl, methoxycarbonyl, acetyl, propionyl, butyryl and isobutyryl groups and the alkyl, aralkyl or aryl-esters thereof, carbamoyl groups, oxycarbonyloxy groups, such as ethoxycarbonyloxy group, carboximidic acid groups, thiocarboxy groups and the like.

Z denotes $-CH_2-$, $-CH_2-CH_2-$, $-CH_2-CH_2-CH_2-$, $-CH_2-CH=CH-$, $-CH=CH-CH_2-$, $-CH_2-CO-$, $-CO-CH_2-$, $-NHCO-$, $-CONH-$, $-NHCH_2-$, $-CH_2NH-$, $-N=CH-$, $-NHCH-$, $-CH_2-CH_2-NH-$, $-CH=CH-$, $>N-R_3$, $>C=O$, $>S(O)_m$, wherein m denotes an integer from 0 to 2.

$R_2'$ denotes hydrogen, an optionally polyfluorinated $C_{1-6}$-alkyl group such as methyl, an ethyl, a propyl, an isopropyl, a butyl, an isobutyl, a tert.-butyl, a pentyl, an isopentyl, a hexyl or an isohexyl group, a group $CF_3$ or $C_2F_5$, an aralkyl group having 1 to 4 carbon atoms in the alkyl chain, such as a benzyl group, an ethylphenyl group, an aryl group, such as a phenyl group, or a heteroaryl group, such as a pyridyl group, a pyridazinyl group, a thienyl group, a thiazolyl group or an isothiazolyl group. $R_2'$ may also denote a group $-(CH_2)_n-X$ wherein X denotes halogen, $-NO_2$, $-OR_4$, $-COR_4$, $-CO_2R_4$, $-OCO_2R_4$, $-CN$, $-CONR_4OR_5$, $-CONR_4R_5$, $-SR_4$, $-S(O)R_4$, $-S(O)_2R_4$, $-NR_4R_5$, $-NHC(O)R_4$, $-NHS(O)_2R_4$, and n is an integer from 0 to 6.

$R_4$ and $R_5$ independently of each other denote hydrogen, $C_{1-6}$-alkyl, aralkyl having 1 to 4 carbon atoms in the alkyl chain, such as benzyl, ethylphenyl or aryl, such as phenyl.

Furthermore, $R_2$ and $R_3$ together with the N-atom may s denote a three- to seven-membered, saturated, partially or totally unsaturated heterocycle having one or more heteroatoms N, O or S, which may optionally be substituted by oxo, an alkyl, alkylaryl or aryl group or a group $(CH_2)_n-X$, wherein X denotes halogen, $-NO_2$, $-OR_4$, $-COR_4$, $-CO_2R_4$, $-OCO_2R_4$, $-CN$, $-CONR_4OR_5-$, $-CONR_4R_5$, $-SR_4$, $-S(O)R_4$, $-S(O)_2R_4$, $-NR_4R_5$, $-NHC(O)R_4$, $-NHS(O)_2R_4$, and n is an integer from 0 to 6.

Examples of such rings include the morpholyl group, the aziridinyl group, the azetidinyl group, the pyridyl group, the pyrazolyl group, the thiazolyl group and the like.

$R_6$ denotes a straight-chained or branched $C_{1-4}$-alkyl group such as methyl, ethyl, propyl, isopropyl, butyl, isobutyl or tert.-butyl. These groups may optionally be mono- or polysubstituted by halogen, e.g. Cl, F or Br, or by alkoxy, such as methoxy, ethoxy and the like.

The compounds according to the invention wherein B denotes a group of formula IIa may be prepared by reacting a compound of formula III

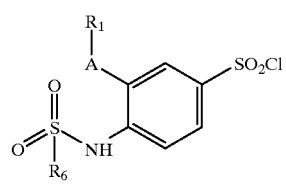

III with a compound of formula IV $HNR_2R_3$                                                                IV or a salt thereof.

The reaction is preferably carried out in the presence of a diluent or solvent which is inert under reaction conditions, such as dioxan, tetrahydrofuran or the like. The reaction temperature ranges from about $-10°$ C. to the reflux temperature of the solvent or diluent, preferably from $-10°$ C. to ambient temperature.

The starting compounds of formula III may be prepared, for example, according to the following reaction scheme or by other methods known to those skilled in the art.

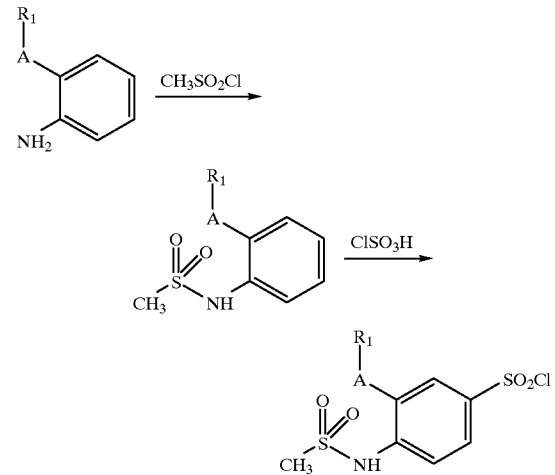

Moreover, the compounds of formula I wherein B denotes a group IIa may be prepared by the following reaction scheme:

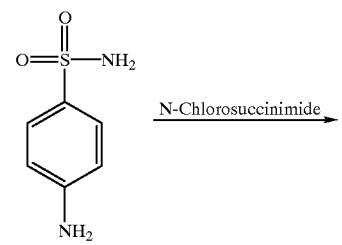

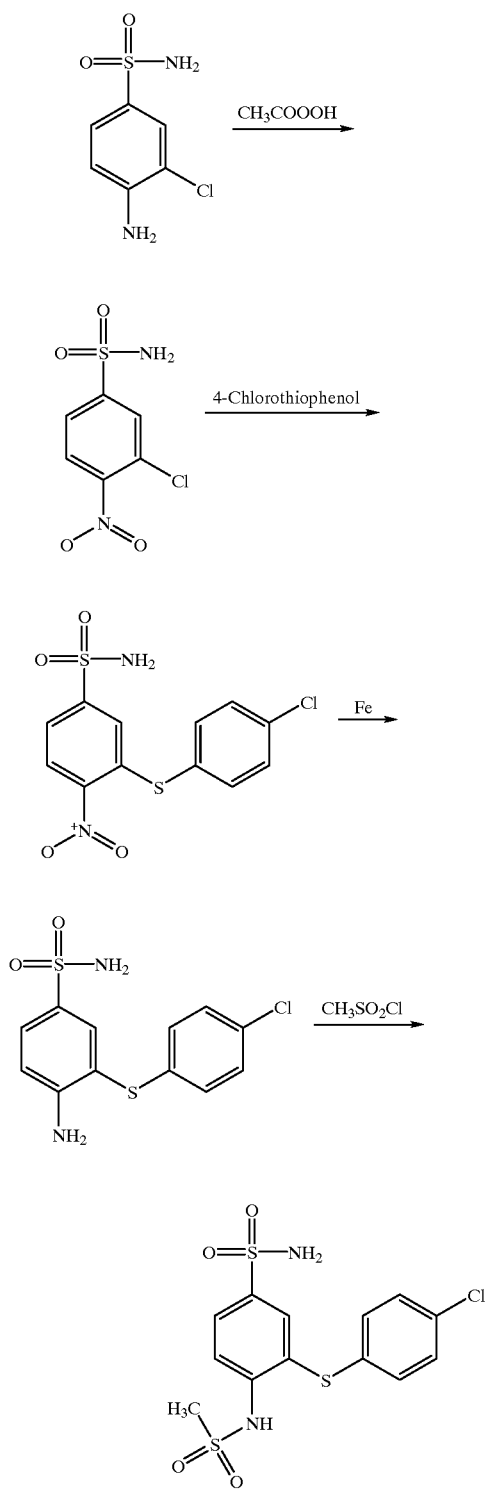

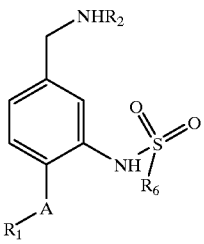

with an acid halide of sulphur, e.g. sulphuryl chloride.

The reaction is preferably carried out in the presence of a diluent or solvent which is inert under reaction conditions, such as dioxan, tetrahydrofuran or the like, preferably in the presence of a catalyst, e.g. aluminium chloride. The reaction temperature ranges from about $-10°$ C. to the reflux temperature of the solvent or diluent, preferably from $-10°$ C. to ambient temperature.

The starting compounds of formula V may be prepared, for example, according to the following reaction plan or by other methods known to those skilled in the art.

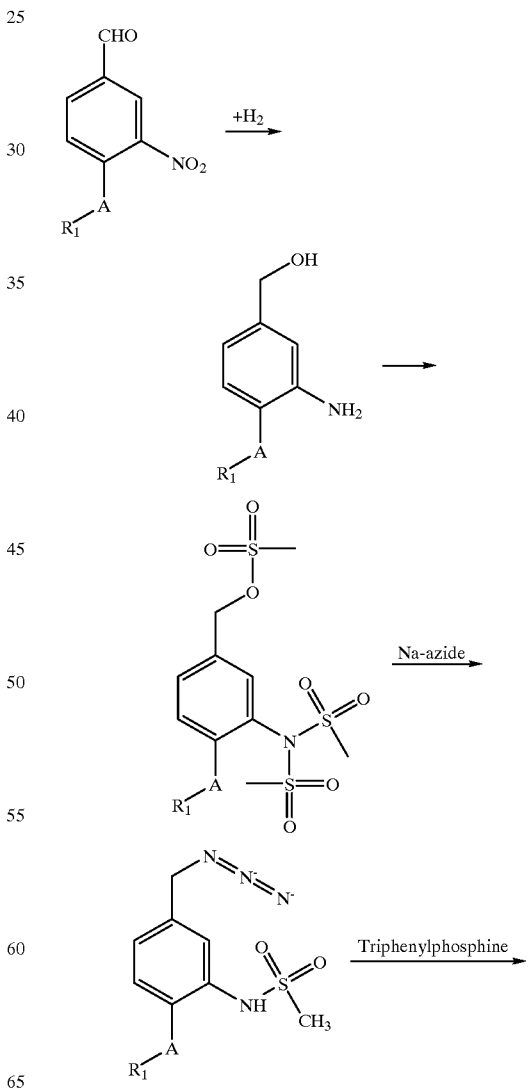

The compounds according to the invention wherein B denotes a group of formula IIb may be prepared by reacting a compound of formula V 7
-continued

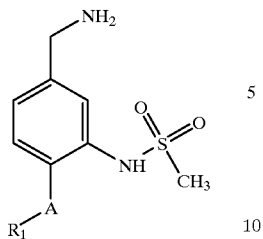

Scheme 2

The compounds of formula I according to the invention wherein B denotes a group of formula IIb may alternatively be prepared as follows:

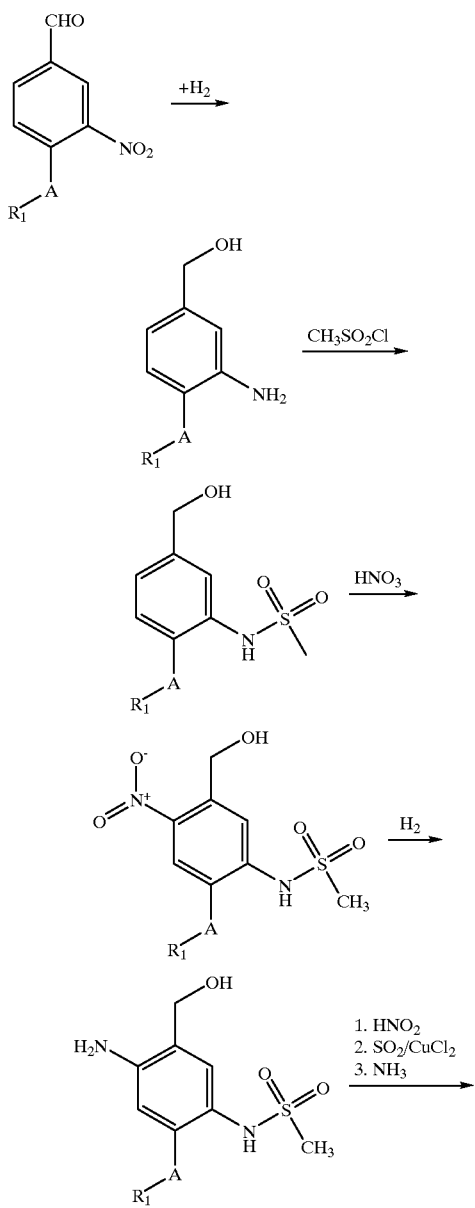

8
-continued

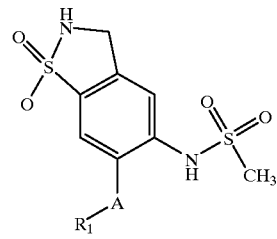

The compounds of formula I obtained as described above are acidic or basic compounds and can be converted into their pharmaceutically acceptable salts with inorganic or organic bases or acids in the usual way. Salt formation may be carried out, for example, by dissolving a compound of formula I in a suitable solvent such as water, acetone, acetonitrile, benzene, dimethylformamide, dimethylsulphoxide, chloroform, dioxan, methanol, ethanol, hexanol, ethyl acetate or in an aliphatic ether, such as diethylether, or mixtures of such solvents, adding an at least equivalent quantity of the desired base or acid, mixing thoroughly and, after salt formation has ended, filtering off the precipitated salt, lyophilising it or distilling the solvent off in vacuo. If desired, the salts may be recrystallised after isolation.

Pharmaceutically acceptable salts are those with inorganic acids such as hydrochloric acid, hydrobromic acid, sulphuric acid, phosphoric acid or nitric acid, or with organic acids such as citric acid, tartaric acid, maleic acid, fumaric acid, succinic acid, malic acid, methanesulphonic acid, aminosulphonic acid, acetic acid, benzoic acid and the like. Pharmaceutically acceptable salts are, for example, metal salts, particularly alkali metal or alkaline earth metal salts such as sodium, potassium, magnesium or calcium salts. Other pharmaceutical salts include, for example, the readily crystallising ammonium salts. These are derived from ammonia or organic amines such as mono-, di- or tri- lower (alkyl, cycloalkyl or hydroxyalkyl) amines, lower alkylenediamines or hydroxy- or aryl-lower alkylammonium bases, e.g. methylamine, diethylamine, triethylamine, ethylenediamine, tris-(hydroxymethyl)-aminomethane, benzyltrimethylammonium-hydroxide and the like.

The new compounds are readily soluble and, by virtue of their selective effect on the enzyme cyclooxygenase II, they exhibit excellent anti-inflammatory, analgesic, anti-pyretic and anti-allergic properties, without having the extremely undesirable side effects of known anti-inflammatories.

In view of these pharmacological properties the new compounds may be used on their own or in conjunction with other active substances in the form of conventional galenic preparations as therapeutic agents for treating disorders or diseases which may be prevented, treated or cured by inhibiting cyclooxygenase II.

These disorders or diseases include pain, fever and inflammation of various kinds, such as rheumatic fever, symptoms which accompany influenza, influenza-like or other viral infections, headache and aching limbs, toothache, sprains, neuralgia, muscle inflammation, joint inflammation, inflammation of the skin of the joint, arthritis, rheumatoid arthritis, other rheumatic forms of inflammation of a degenerative type such as osteoarthritis, gout, stiffening of the joints, spondylitis, bursitis, burns and injuries.

The invention therefore relates to pharmaceutical preparations which contain the compounds of formula I according to the invention or the salts thereof, on their own or mixed with other therapeutically useful active substances, as well as conventional galenic adjuvants and/or carriers or diluents.

The compounds according to the invention may be administered orally in the form of tablets or capsules which contain a dosage unit of the compound together with excipients and diluents such as maize starch, calcium carbonate, dicalcium phosphate, alginic acid, lactose, magnesium stearate, primogel or talc. The tablets are prepared in the usual way by granulating the ingredients and compressing, whilst capsules are prepared by packing into hard gelatine capsules of suitable size.

Another form of administering the compounds according to the invention is in suppositories which contain excipients such as beeswax derivatives, polyethylene glycol or polyethylene glycol derivatives, linoleic or linolenic acid esters, together with a single dose of the compound, and these may be administered by rectal route.

The compounds according to the invention may also be administered parenterally, e.g. by intramuscular, intravenous or subcutaneous injection. For parenteral administration they are best used in the form of a sterile aqueous solution which may contain other dissolved substances such as tonic agents, agents for adjusting the pH, preservatives and stabilisers. The compounds may have distilled water added to them and the pH may be adjusted to 3 to 6 using citric acid, lactic acid or hydrochloric acid, for example. Sufficiently dissolved substances such as dextrose or saline solution may be added to render the solution isotonic. Moreover, preservatives such as p-hydroxybenzoates and stabilisers such as EDTA may be added to ensure sufficient shelf-life and stability of the solution. The solution thus obtained can then be sterilised and transferred into sterile ampoules of a suitable size to contain the required volume of solution. The compounds according to the invention may also be administered by infusion of a parenteral formulation as described above.

Moreover, the compounds according to the invention may be formulated for topical or transdermal application with suitable excipients and/or carriers, emulsifiers, surfactants and/or diluents, e.g. vaseline, olive oil, groundnut oil, sesame oil, soya oil, water, glycols, cetyl stearyl esters, triglycerides, cetaceum, miglyol and the like to obtain ointments, creams, gels or plasters or, for example, with talc to obtain powders.

For oral administration in humans it is assumed that the daily dose of a compound according to the invention will be within the range from 0.01 to 1000 mg per day for a typical adult weighing 70 kg. Therefore, tablets or capsules may usually contain 0.003 to 300 mg of active compound, e.g. 0.1 to 50 mg, for oral administration up to three times a day. For parenteral administration the dosage may be in the range from 0.01 to 1000 mg per 70 kg per day, for example about 5 mg.

EXAMPLE 1

3-(2,4-Dichlorophenoxy)-4-methylsulphonylamino-benzenesulphonamide

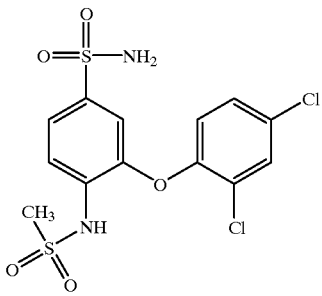

(a) 2-(2,4-Dichlorophenoxy)-nitrobenzene

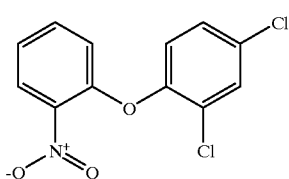

2-Chloronitrobenzene (20.0 g, 126.94 mmol) were dissolved in xylene (400 ml) and 2,4-dichlorophenol (22.7 g, 139.0 mmol) was added. Then potassium carbonate (19.2 g, 139.0 mmol) was added and the resulting mixture was refluxed for 10 hours. After the further addition of 2,4-dichlorophenol (6.8 g, 41.7 mmol) and potassium carbonate (5.8 g, 42.0 mmol) the mixture was refluxed overnight. After cooling, the solid residue was filtered off and the solvent was evaporated off. The residue was recrystallised from ethanol. Yield: 26.2 g=72.7% $^{13}$C (100 MHz, CDCl$_3$) δ 150.01, 149.81, 140.81, 134.28, 130.86, 130.77, 128.38, 126.99, 126.02, 123.73, 121.79, 119.22

(b) 2-(2,4-Dichlorophenoxy)-aniline

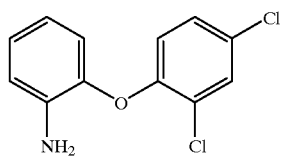

2-(2,4-Dichlorophenoxy)-nitrobenzene (10.0 g, 35.2 mmol) were dissolved in dioxan (100 ml and a suspension of Raney nickel in water (20 g) was added. The mixture was hydrogenated for 6 hours at 3.5 to 4.0 bar. It was then filtered and the solvent was eliminated. Yield: 8.9 g=100% $^{13}$C (100 MHz, CDCl$_3$) δ 151.79, 142.68, 138.29, 130.31, 128.24, 127.91, 125.45, 125.04, 119.46, 118.89, 118.78, 116.68

(c) 2-(2,4-Dichlorophenoxy)-N-methylsulphonylanilide

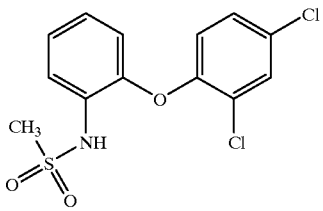

2-(2,4-Dichlorophenoxy)-aniline (8.9 g, 35.02 mmol) were dissolved in dichloromethane (200 ml) and triethylamine (14.7 g, 145 mmol) was added at 0° C. At this temperature, methanesulphonic acid chloride (4.0 g, 35.02 mmol) was added dropwise. After 1 hour at 0° C., methanesulphonic acid chloride (4.0 g, 35.02 mmol) was added dropwise once more and stirring was continued for another hour. The mixture was poured onto saturated $NaHCO_3$ solution and the phases were separated. The aqueous phase was extracted twice more with dichloromethane and the combined organic phases were dried over $MgSO_4$. After evaporation of the solvent the residue was dissolved in dioxan (100 ml) and methanol (100 ml) and cooled to 0° C. 2N sodium hydroxide solution in water (100 ml, 200 mmol) was added dropwise and the solution was stirred for 30 minutes at 0°. The mixture was acidified with $KHSO_4$ and extracted with ethyl acetate. It was dried over $MgSO_4$ and the solvent was evaporated off. The residue was recrystallised from ethanol. Yield: 9.28 g=80% $^{13}C$ (100 MHz, $CDCl_3$) δ 149.68, 147.24, 130.88, 130.78, 128.51, 127.30, 126.98, 125.86, 124.44, 122.40, 122.19, 116.09, 39.73

(d) 3-(2,4-Dichlorophenoxy)-4-methylsulphonylaminobenzenesulphonic acid chloride

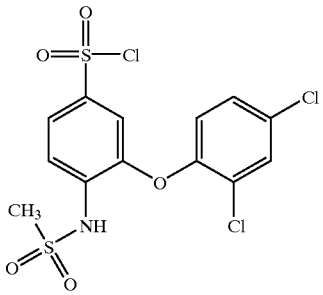

Chlorosulphonic acid (0.80 ml, 12.0 mmol) was dissolved in chloroform (10 ml) and cooled to 0° C. A solution of 2-(2,4-dichlorophenoxy)-N-methylsulphonylanilide (1.0 g, 3.01 mmol) in chloroform (5 ml) was added dropwise and the solution was stirred for 30 minutes at 0° C. and for 2 hours at ambient temperature. After the addition of water, the mixture was extracted with chloroform, dried over $MgSO_4$ and concentrated by rotary evaporation. The residue was purified by chromatography (dichloromethane/petroleum ether—silica gel). Yield: 0.50 g=38.8% $^{13}C$ (100 MHz, $CDCl_3$) δ 147.79, 145.65, 139.20, 133.80, 132.84, 131.51, 129.21, 127.39, 123.43, 118.26, 112.98, 40.85

(e) 3-(2,4-Dichlorophenoxy)-4-methylsulphonylaminobenzenesulphonamide

A mixture of dioxan (20 ml) and conc. ammonium chloride (20 ml) was cooled to 0° C. and a solution of 3-(2,4-dichlorophenoxy)-4-methylsulphonyl-aminobenzenesulphonic acid chloride (0.49 g, 1.14 mmol) in dioxan (10 ml) was added dropwise. The solution was stirred for 1 hour at 0° C. and then acidified with conc. HCl. It was extracted with ethyl acetate, dried over $MgSO_4$ and concentrated by rotary evaporation. The residue was recrystallised from chloroform. Yield: 0.37 g=80% $^{13}C$ (100 MHz, DMSO-$d_6$) δ 149.96, 147.96, 141.03, 131.42, 130.40, 129.60, 129.21, 126.33, 123.97, 123.03, 121.57, 114.05, 40.99

EXAMPLE 2

6-(2,4-Dichlorophenoxy)-5-methylsulphonylamino-2H-1,2-benzothiazolidine-1,1-dioxide

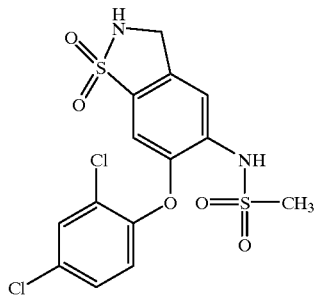

(a) 4-(2,4-Dichlorophenoxy)-3-nitrobenzaldehyde

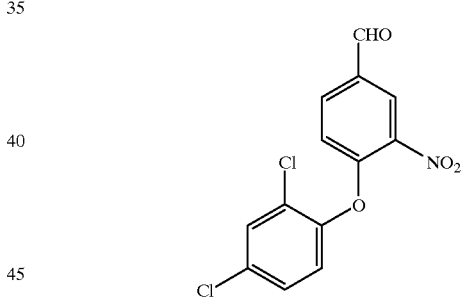

4-Chloro-3-nitrobenzaldehyde (47.12 g, 253.92 mmol) were dissolved in xylene (400 ml) and 2,4-dichlorophenol (45.32 g, 278.03 mmol) was added. Then potassium carbonate (38.40 g, 277.84 mmol) was added and the resulting mixture was refluxed for 6 hours. After cooling, the solid residue was filtered off and the solvent was evaporated off. The residue was dissolved in $CH_2Cl_2$, extracted several times with 1N NaOH and dried over $MgSO_4$. After evaporation of the solvent the remainder was dried in vacuo. The product could be used for the next step without further purification. Yield: 74.5 g 94% $^{13}C$ (100 MHz, $CDCl_3$) δ 188.39, 154.42, 148.22, 140.21, 134.28, 132.51, 131.30, 131.19, 128.92, 127.74, 127.72, 123.51, 117.80

(b) 2-(2,4-Dichlorophenoxy)-5-hydroxymethylaniline

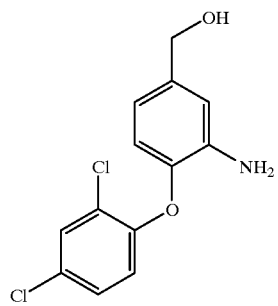

4-(2,4-Dichlorophenoxy)-3-nitrobenzaldehyde (15.0 g, 48.06 mmol) was dissolved in dioxan (150 ml) and a suspension of Raney nickel in water (10.0 g) was added. The mixture was hydrogenated at 3.5 to 4.0 bar until the uptake of hydrogen had ended. It was then filtered and the solvent was removed. Yield: 13.5 g=99% $^{13}$C (100 MHz, CDCl$_3$) δ 151.69, 142.15, 138.29, 130.34, 128.38, 127.94, 125.09, 119.30, 119.01, 117.26, 115.23, 64.91

(c) 2-(2,4-Dichlorophenoxy)-5-hydroxymethyl-N-methylsulphonylanilide

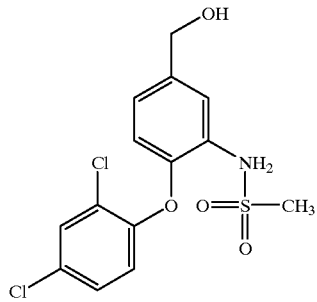

2-(2,4-Dichlorophenoxy)-5-hydroxymethylaniline (6.36 g, 22.38 mmol) was dissolved in pyridine (50 ml) and at −20° C. methanesulphonic acid chloride (2.86 g; 25.0 mmol) was added dropwise. The mixture came up to ambient temperature overnight, after which the solvent was removed by rotary evaporation. The residue was dissolved in ethyl acetate and extracted with 1N HCl. The combined organic phases were dried over MgSO$_4$ and after evaporation of the solvent the residue was purified by chromatography (CHCl$_3$/MeOH 19/1, silica gel). Yield: 5.60 g=69% $^{13}$C (100 MHz, CDCl$_3$) δ 149.68, 146.49, 137.49, 130.92, 130.86, 128.52, 127.23, 126.92, 124.33, 122.10, 120.86, 116.16, 64.43, 39.87

(d) 2-(2,4-Dichlorophenoxy)-5-acetoxymethyl-4-nitro-N-methylsulphonylanilide

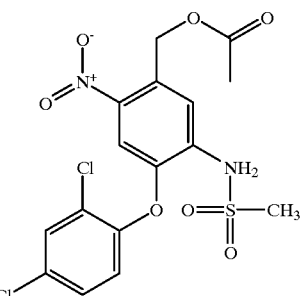

2-(2,4-Dichlorophenoxy)-5-hydroxymethyl-N-methylsulphonylanilide (1.00 g, 2.76 mmol) was dissolved at 110° C. in glacial acetic acid (10 ml) and 65% of HNO$_3$ (0.21 ml, 3.0 mmol) were slowly added dropwise. The mixture was heated to 110° C. for 2 hours. After cooling, CHCl$_3$ (100 ml) was added and extraction was carried out with NaHCO$_3$ solution. The organic phase was dried over MgSO$_4$ and the solvent was eliminated by rotary evaporation. The residue was further processed without purification. Yield: 1.11 g=96% $^{13}$C (100 MHz, CDCl$_3$) δ 170.40, 147.99, 144.96, 142.35, 132.70, 132.43, 131.42, 129.64, 129.13, 127.42, 123.43, 117.81, 111.75, 62.67, 40.59, 20.71

(e) 2-(2,4-Dichlorophenoxy)-5-hydroxymethyl-4-nitro-N-methylsulphonylanilide

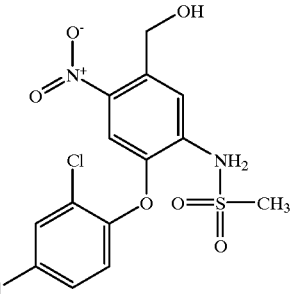

2- (2,4-Dichlorophenoxy) -5-acetoxymethyl-4-nitro-N-methylsulphonylanilide (1.05 g, 2.49 mmol) was dissolved at 0° C. in dioxan (20 ml), MeOH (20 ml) and water (20 ml) and 2N NaOH (15 ml, 30 mmol) was added. The resulting mixture was stirred for 3 hours at 0° C., acidified with 1N HCl and extracted with ethyl acetate. The combined organic phases were dried over MgSO$_4$ and the solvent was eliminated by rotary evaporation. The residue was purified by chromatography (CHCl$_3$/MeOH 19/1, silica gel). Yield: 0.88 g=87% $^{13}$C (100 MHz, CDCl$_3$) δ 150.10, 145.06, 141.71, 136.05, 134.31, 130.42, 129.52, 129.14, 125.95, 122.46, 120.54, 113.50, 59.91, 40.98

(f) 4-Amino-2-(2,4-dichlorophenoxy)-5-hydroxymethyl-N-methylsulphonylanilide

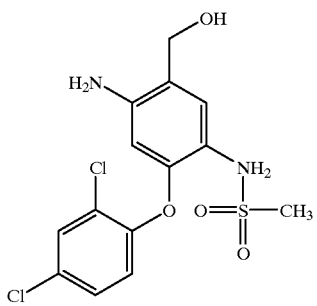

2-(2,4-Dichlorophenoxy)-5-hydroxymethyl-4-nitro-N-methylsulphonylanilide (0.88 g, 2.16 mmol) was dissolved in dioxan (50 ml) and a suspension of Raney nickel in water (1.0 g) was added. The mixture was hydrogenated at 3.5 to 4.0 bar until the uptake of hydrogen had ended. It was then filtered and the solvent was removed. The residue was purified by chromatography (CHCl$_3$/MeOH 19/1, silica gel). Yield: 0.70 g=86% $^{13}$C (100 MHz, CDCl$_3$) δ 150.31, 149.71, 146.23, 130.85, 130.71, 128.50, 128.05, 126.92, 122.08, 120.65, 115.85, 103.15, 63.53, 39.30

(g) 6-(2,4-Dichlorophenoxy)-5-methylsulphonylamino-2H-1,2-benzothiazolidine-1,1-dioxide 4-Amino-2-(2,4-dichlorophenoxy)-5-hydroxymethyl-N-methylsulphonylanilide (0.70 g, 1.86 mmol) was suspended at 0° C. in 8M hydrotetrafluoroboric acid (15 ml) and a solution of NaNO$_2$ (0.14 g, 2.0 mmol) in water (1 ml) was added. This was stirred for 30 minutes and at 0° C. the suspension was added to a mixture of saturated CuCl$_2$ solution in water (10 ml) and saturated SO$_2$ solution in HOAc (50 ml). After 30 minutes at this temperature stirring was continued for a further 30 minutes at ambient temperature, then the mixture was diluted with water, extracted with ethyl acetate, dried over MgSO$_4$ and the solvent was removed by rotary evaporation. The residue was dissolved in dioxan (2 ml) and added dropwise to a mixture of dioxan (20 ml) and conc. ammonium chloride (20 ml). The solution was stirred for 1 hour at 0° C. and then acidified with conc. HCl. It was extracted with ethyl acetate, dried over MgSO$_4$ and concentrated by rotary evaporation. The residue was purified by chromatography (CH$_2$Cl$_2$/ethyl acetate 9/1) Yield: 0.24 g=32% $^{13}$C (100 MHz, CDCl$_3$) δ 148.31, 147.37, 142.82, 133.96, 132.37, 131.29, 131.19, 129.01, 127.49, 123.53, 112.91, 109.41, 78.52, 40.29

EXAMPLE 3

8-(2,4-Dichlorophenoxy)-7-methylsulphonylamino-3,4,5-dihydro-2-H-1,2-benzothiazepin-1,1-dioxide

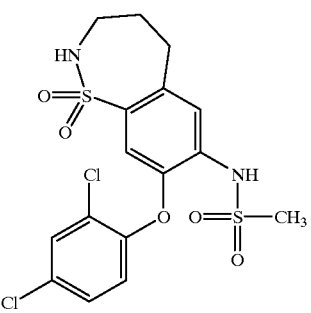

(a) 4-(2,4-Dichlorophenoxy)-3-nitrobenzaldehyde was prepared as described in Example 2a)

(b) Methyl 4-(2,4-dichlorophenoxy)-3-nitro-E-cinnamate

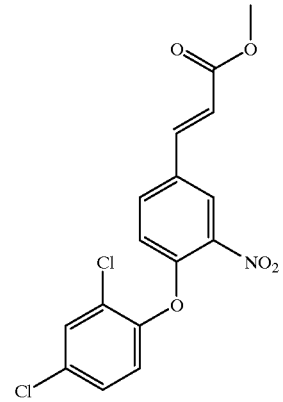

Trimethylphosphonoacetate (19.60 g, 107.62 mmol) was dissolved in THF (250 ml) and at −70° C. n-BuLi (67.0 ml, 107.2 mmol) was added dropwise and the mixture was stirred for 15 minutes. A solution of 4-(2,4-dichlorophenoxy)-3-nitrobenzaldehyde (29.0 g, 92.9 mmol) in THF (200 ml) was added dropwise and stirred for 1 hour at −70° C. Then the resulting mixture was poured onto phosphate buffer (pH 7, 400 ml), extracted with CH$_2$Cl$_2$, dried over MgSO$_4$ and concentrated by rotary evaporation. The residue was recrystallised from ethanol. Yield: 31.3 g=92% $^{13}$C (100 MHz, CDCl$_3$) δ 165.56, 150.98, 149.15, 141.17, 133.19, 131.60, 131.01, 130.23, 128.63, 127.36, 125.20, 122.64, 119.98, 118.76, 51.93

(c) Methyl 4-(2,4-dichlorophenoxy)-3-aminophenylpropionate

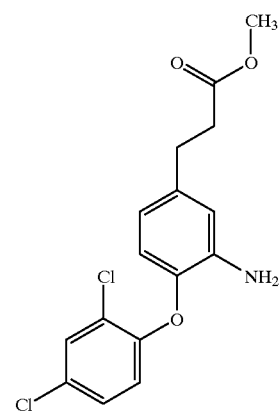

Methyl 4-(2,4-dichlorophenoxy)-3-nitro-E-cinnamate (31.30 g, 85.01 mmol) was dissolved in dioxan (60 ml) and a suspension of Raney nickel in water (31.0 g) was added. The mixture was hydrogenated at 3.5 to 4.0 bar until the uptake of hydrogen had ended. It was then filtered and the solvent was removed. Yield: 29.9 g=99.9% $^{13}$C (100 MHz, CDCl$_3$) δ 173.30, 151.92, 141.05, 138.22, 137.99, 130.26, 128.07, 127.87, 124.85, 119.64, 118.48, 116.51, 51.59, 35.65, 30.47

(d) Methyl 4-(2,4-dichlorophenoxy)-3-methylsulphonylamino-phenylpropionate

The synthesis was carried out analogously to Example 2(c). The product was purified by chromatography (petroleum ether/ethyl acetate 8/3, silica gel). $^{13}$C (100 MHz, CDCl$_3$) δ 172.94, 149.90, 145.54, 137.17, 130.83, 130.57, 128.44, 127.30, 126.78, 125.60, 122.08, 121.83, 116.35, 51.66, 39.70, 35.52, 30.32

(e) Methyl 4-(2,4-dichlorophenoxy)-3-methylsulphonyl-amino-6-nitro-phenylpropionate The synthesis was carried out analogously to Example 2(d). The product was purified by chromatography (CH$_2$Cl$_2$, silica gel). $^{13}$C (100 MHz, CDCl$_3$) δ 172.63, 148.33, 144.38, 143.93, 132.80, 132.24, 132.04, 131.26, 129.00, 127.31, 123.19, 121.48, 111.99, 51.79, 40.52, 34.33, 28.56

(f) 1-[4-(2,4-Dichlorophenoxy)-3-methylsulphonylamino-6-amino-phenyl]-3-propanol

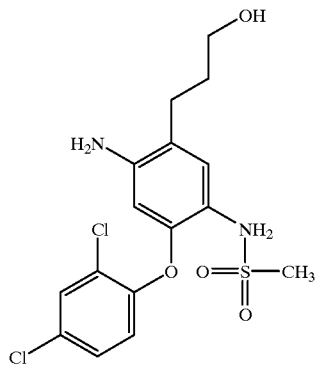

Methyl 4-(2,4-dichlorophenoxy)-3-methylsulphonylamino-6-nitro-phenylpropionate (11.3 g, 24.4 mmol) was dissolved in THF (200 ml) and dissolved at 0° C. LiAlH$_4$ (4.0 g, 105.3 mmol) was added in batches and the mixture returned to ambient temperature overnight. It was acidified, extracted with ethyl acetate, dried over MgSO$_4$ and concentrated by rotary evaporation. Since only the ester function has been reduced, the residue was hydrogenated as described in Example 2(f) and purified by chromatography (CH$_2$Cl$_2$/MeOH 9/1, silica gel). Yield: 5.84 g=52% $^{13}$C (100 MHz, DMSO-d$_6$) δ 151.46, 150.22, 146.71, 130.66, 129.80, 128.72, 127.85, 125.26, 121.67, 121.36, 114.83, 103.19, 60.28, 40.17, 31.66, 26.16

(g) 8-(2,4-Dichlorophenoxy)-7-methylsulphonylamino-3,4,5-dihydro-2-H-1,2-benzothiazepin-1,1-dioxide Synthesis was carried out analogously to Example 2(g). The residue after amidation was taken up in toluene once more and refluxed for 2 hours. After evaporation of the solvent the residue was purified by chromatography (CH$_2$Cl$_2$, silica gel) $^{13}$C (100 MHz, CDCl$_3$) δ 148.83, 145.24, 142.86, 135.40, 131.69, 131.13, 130.00, 128.82, 127.11, 122.78, 122.13, 113.52, 67.55, 40.24, 31.71, 29.17

EXAMPLE 4

6-(Phenoxy)-5-methylsulphonylamino-2H-1,2-benzothiazolidin-1,1-dioxide

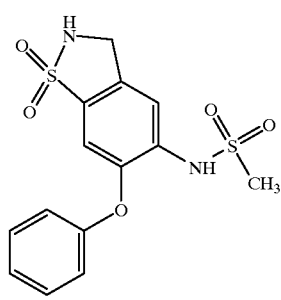

a) 4-Phenoxy-3-nitrobenzaldehyde

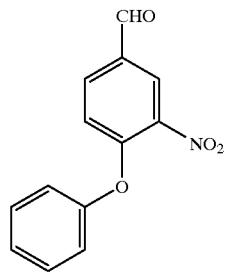

Synthesis was carried out analogously to Example 2(a). The residue was recrystallised from ethanol.

b) 2-Phenoxy-5-hydroxymethylaniline

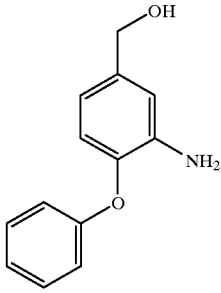

Synthesis was carried out analogously to Example 2(b).

c) 5-Hydroxymethyl-2-phenoxy-N-methylsulphonylanilide

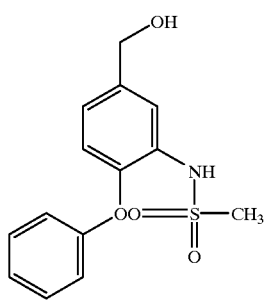

Synthesis was carried out analogously to Example 2(c).

d) 5-Hydroxymethyl-4-nitro-2-phenoxy-N-methylsulphonylanilide

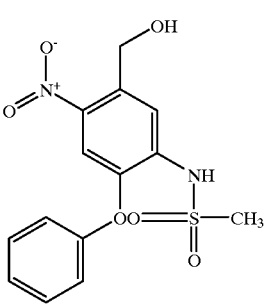

Synthesis was carried out analogously to Examples 2(d) and 2(e).

e) 4-Amino-5-hydroxymethyl-2-phenoxy-N-methylsulphonylanilide

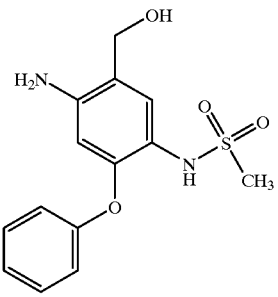

Synthesis was carried out analogously to Example 2(f).

f) 6-(Phenoxy)-5-methylsulphonylamino-2H-1,2-benzothiazolidin-1,1-dioxide

Synthesis was carried out analogously to Example 2(g). $^{13}$C (100 MHz, CDCl$_3$) δ 159.63, 147.85, 143.17, 134.67, 133.77, 130.64, 129.46, 124.41, 120.68, 113.95, 75.20, 41.04

EXAMPLE 5

3-(2,4-Difluorophenoxy)-4-methylsulphonylamino-benzenesulphonamide

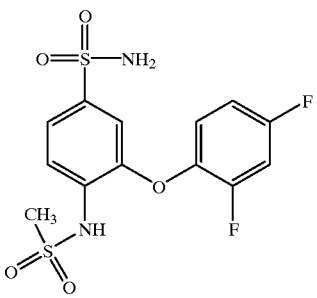

(a) 2-(2,4-Difluorophenoxy)-nitrobenzene

Synthesis was carried out analogously to Example 1(a). For purification the product was chromatographed with CH$_2$Cl$_2$/petroleum ether 1/9 over silica gel. $^{13}$C (100 MHz, CDCl$_3$) δ 160.87, 160.77, 158.41, 158.31, 155.40, 155.27, 152.88, 152.76, 150.71, 140.37, 138.59, 138.56, 138.51, 138.48, 134.18, 125.92, 123.17, 123.05, 122.96, 117.93, 111.95, 111.91, 111.72, 111.68, 106.05, 105.84, 105.78, 105.57

(b) 2-(2,4-Difluorophenoxy)-aniline

Synthesis was carried out analogously to Example 1(b). $^1$H (400 MHz, CDCl$_3$) δ 159.52, 159.42, 157.09, 156.98, 154.88, 154.76, 152.38, 152.26, 144.06, 140.73, 140.70, 140.62, 140.58, 137.71, 124.60, 120.90, 120.88, 120.81, 120.79, 118.66, 117.55, 116.48, 111.22, 111.18, 111.00, 110.95, 105.55, 105.33, 105.28, 105.06

(c) 2-(2,4-Difluorophenoxy)-N-methylsulphonylanilide

Synthesis was carried out analogously to Example 1(c). The product was used for further synthesis without being purified. $^{13}$C (100 MHz, CDCl$_3$) δ 160.82, 160.72, 158.36, 158.22, 155.58, 155.47, 153.08, 152.96, 148.18, 138.52, 138.48, 138.40, 138.36, 129.72, 126.80, 125.81, 124.01, 123.37, 123.36, 123.28, 123.26, 122.27, 114.92, 111.97, 111.93, 111.74, 111.70, 106.12, 105.91, 105.86, 105.64, 39.45

(d) 3-(2,4-Difluorophenoxy)-4-methylsulphonylamino-benzenesulphonamide

Chlorosulphonic acid (3.6 ml, 53.6 mmol) was dissolved in chloroform (40 ml) and cooled to 0° C. A solution of 2-(2,4-difluorophenoxy)-N-methylsulphonyl-anilide (4.02 g, 13.4 mmol) in chloroform (20 ml) was added dropwise and the solution was stirred for 30 minutes at 0° C. and for 2 hours at ambient temperature. Then phosphorus pentachloride (11 g, 53.6 mmol) was added and stirring was continued for 2 hours. The unreacted phosphorus pentachloride was filtered off and the filtrate was extracted with ice water, dried over MgSO$_4$ and concentrated by rotary evaporation. The residue (7.1 g) was dissolved in dioxane (70 ml) and ammonia was piped in at 10° C. After 1.5 hours ethyl acetate (100 ml) was added and the mixture was extracted with 1N HCl. The organic phase was dried over MgSO$_4$ and concentrated by evaporation. The residue was purified by chromatography (silica gel, CH$_2$Cl$_2$/ethyl acetate 19/1) Yield: 3.9 g=57% $^{13}$C (100 MHz, DMSO-d$_6$) δ 160.21, 160.10, 157.78, 157.67, 155.08, 154.95, 152.59, 152.46, 148.84, 141.02, 138.51, 138.47, 138.40, 138.36, 130.79, 123.90, 123.84, 121.15, 112.87, 112.67, 112.64, 112.45, 112.41, 106.35, 106.13, 106.07, 105.85, 40.88

EXAMPLE 6

3-(2,4-Difluorothiophenoxy)-4-methylsulphonylamino-benzenesulphonamide

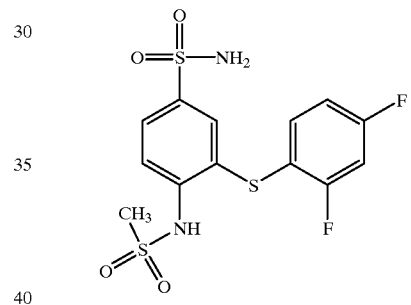

(a) 2-(2,4-Difluorothiophenoxy)-nitrobenzene

Synthesis was carried out analogously to Example 1(a). For purification the product was crystallised from petroleum ether. $^{13}$C (100 MHz, CDCl$_3$) δ 166.16, 166.05, 165.06, 164.93, 163.63, 163.52, 162.54, 162.42, 145.18, 139.01, 139.00, 138.91, 137.22, 133.69, 127.38, 126.05, 125.44, 114.06, 114.02, 113.87 113.83, 113.27, 113.23, 113.05, 113.01, 105.78, 105.52, 105.26

(b) 2-(2,4-Difluorothiophenoxy)-aniline

Synthesis was carried out analogously to Example 1(b). $^{13}$C (100 MHz, CDCl$_3$) δ 162.90, 162.80, 161.15, 161.03, 160.44, 160.33, 158.70, 158.58, 148.88, 137.31, 131.35, 130.37, 130.34, 130.28, 130.25, 118.92, 115.46, 113.22, 112.04, 112.01, 111.83, 111.79, 104.46, 104.02, 103.95

(c) 2-(2,4-Difluorothiophenoxy)-N-methylsulphonylanilide

Synthesis was carried out analogously to Example 1(c). The product was used for further synthesis without being purified. $^{13}$C (100 MHz, CDCl$_3$) δ 164.25, 164.13, 162.42, 162.30, 161.75, 161.62, 160.42, 160.30, 138.63, 136.09, 133.27, 133.16, 131.09, 125.37, 119.82, 112.62, 112.59, 112.41, 112.37, 105.27, 105.01, 104.75, 39.70

(d) 3-(2,4-Difluorothiophenoxy)-4-methylsulphonyl-aminobenzenesulphonamide

Synthesis was carried out analogously to Examples 1(d) and 1(e). The residue was recrystallised from ethanol. $^{13}$C (100 MHz, CDCl$_3$) δ 164.61, 164.50, 163.22, 163.09, 162.13, 162.01, 160.75, 160.75, 160.62, 142.33, 138.26, 136.95, 136.86, 132.32, 126.95, 126.38, 125.97, 125.30, 115.18, 115.14, 115.00, 114.96, 113.50, 113.47, 113.29, 113.25, 105.86, 105.59, 105.33, 41.33

EXAMPLE 7

3-(2,4-Dichlorothiophenoxy)-4-methylsulphonylamino-benzenesulphonamide

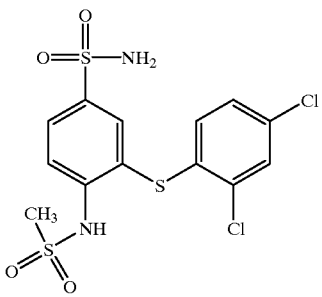

(a) 2-(2,4-Dichlorothiophenoxy)-nitrobenzene

Synthesis was carried out analogously to Example 1(a). For purification the product was crystallised from petroleum ether. $^{13}$C (100MHz, CDCl$_3$) δ 145.45, 139.39, 138.85, 136.44, 134.88, 134.54, 130.59, 129.22, 128.72, 128.42, 126.94, 126.14

(b) 2-(2,4-Dichlorothiophenoxy)-aniline

Synthesis was carried out analogously to Example 1(b). $^{13}$C (100 MHz, CDCl$_3$) δ 149.19, 137.84, 134.88, 131.98, 131.58, 131.16, 129.26, 127.45, 127.23, 119.09, 115.54, 112.13

(c) 2-(2,4-Dichlorothiophenoxy)-N-methylsulphonylanilide

Synthesis was carried out analogously to Example 1(c). The residue was purified by chromatography (CH$_2$Cl$_2$/silica gel). $^{13}$C (100 MHz, CDCl$_3$) δ 139.70, 137.54, 133.33, 132.93, 132.15, 129.89, 128.53, 127.88, 125.50, 119.63, 119.55, 39.88

(d) 3-(2,4-Dichlorothiophenoxy)-4-methylsulphonylamino-benzenesulphonamide

Synthesis was carried out analogously to Examples 1(d) and 1(e). For purification the product was crystallised from (CH$_2$Cl$_2$/MeOH 24/1). $^{13}$C (100 MHz, DMSO-d$_6$) δ 141.78, 141.06, 134.07, 132.82, 132.10, 131.04, 129.72, 128.58, 127.26, 127.25, 124.93, 41.26

EXAMPLE 8

3-(2-Chloro-4-fluorothiophenoxy)-4-methylsulphonylamino-benzene-sulphonamide

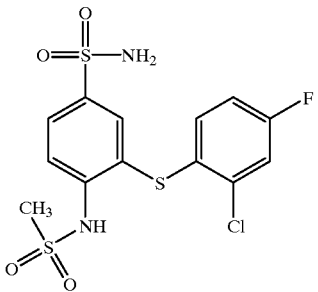

(a) 2-(2-Chloro-4-fluorothiophenoxy)-nitrobenzene

Synthesis was carried out analogously to Example 1(a). For purification the product was crystallised from diethyl-ether. $^{13}$C (100 MHz, CDCl$_3$) δ 165.10, 162.56, 145.17, 141.60, 141.49, 139.54, 139.45, 137.08, 133.68, 127.49, 126.04, 125.89, 125.85, 125.44, 118.74, 118.49, 115.87, 115.65

(b) 2-(2-Chloro-4-fluorothiophenoxy)-aniline

Synthesis was carried out analogously to Example 1(b). 13C (100 MHz, CDCl$_3$) δ 161.79, 159.33, 149.11, 137.72, 131.77, 131.36, 131.33, 127.91, 127.83, 119.04, 117.20, 116.94, 115.50, 114.79, 114.58, 112.90

(c) 2-(2-Chloro-4-fluorothiophenoxy)-N-methylsulphonyl-anilide

Synthesis was carried out analogously to Example 1(c). The residue was recrystallised from ethanol. $^{13}$C (100 MHz, CDCl$_3$) δ 162.71, 160.22, 155.57, 139.30, 136.99, 133.91, 133.80, 131.74, 130.12, 130.03, 129.74, 129.70, 125.50, 120.88, 119.77, 117.90, 117.65, 115.30, 115.08, 39.82

(d) 3-(2-Chloro-4-fluorothiophenoxy)-4-methylsulphonyl-aminobenzenesulphonamide

Synthesis was carried out analogously to Examples 1(d) and 1(e). $^{13}$C (100 MHz, DMSO-d$_6$) δ 163.76, 161.27, 143.05, 137.92, 137.81, 137.28, 137.19, 135.07, 129.49, 126.94, 124.45, 118.46, 118.21, 116.34, 116.12, 41.27

EXAMPLE 9

3-(2,4-Dibromophenoxy)-4-methylsulphonylaminobenzene-sulphonamide

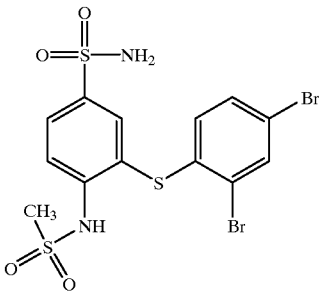

(a) 2-(2,4-Dibromophenoxy)-nitrobenzene

Synthesis was carried out analogously to Example 1(a). For purification the product was crystallised from CH$_2$Cl$_2$/petroleum ether 1/1.5. $^{13}$C (100 MHz, CDCl$_3$) δ 151.84, 149.60, 141.05, 136.46, 134.33, 131.99, 126.03, 123.88, 121.82, 119.60, 118.09, 115.94

(b) 2-(2,4-Dibromophenoxy)-aniline

Synthesis was carried out analogously to Example 1(b). $^{13}$C (100 MHz, CDCl$_3$) δ 153.42, 142.48, 138.37, 135.84, 131.53, 125.61, 119.83, 118.89, 118.81, 116.73, 115.48, 114.01

(c) 2-(2,4-Dibromophenoxy)-N-methylsulphonylanilide

Synthesis was carried out analogously to Example 1(c). The residue was purified by chromatography (CH$_2$Cl$_2$/silica gel) and then recrystallised from ethanol. $^{13}$C (100 MHz, CDCl$_3$) δ 151.42, 146.96, 136.49, 132.12, 127.44, 125.84, 124.59, 122.31, 122.15, 118.60, 118.16, 116.43, 116.05, 39.81

(d) 3-(2,4-Dibromophenoxy)-4-methylsulphonylamino-benzenesulphonamide

Synthesis was carried out analogously to Examples 1(d) and 1(e). The product was purified by chromatography (silica gel; CH$_2$Cl$_2$/MeOH 50/1). $^{13}$C (100 MHz, DMSO-d$_6$) δ 151.67, 147.90, 141.03, 135.77, 132.68, 131.47, 123.99, 123.24, 121.57, 117.54, 116.01, 114.20, 41.05

EXAMPLE 10

3-(Cyclohexyloxy)-4-methylsulphonylaminobenzene-sulphonamide

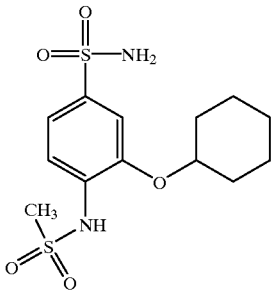

(a) 2-(Cyclohexyloxy)-nitrobenzene

Cyclohexanol (5 ml, 47 mmol) and NaH (2.0 g, 50 mmol) were heated to 70° C. for 1 hour in dioxan (80 ml). After cooling to ambient temperature a solution of 1-fluoro-2-nitrobenzene (7.0 g, 49.6 mmol) in dioxan (20 ml) was added and stirred overnight at ambient temperature. The mixture was poured onto water and extracted with $CH_2Cl_2$. It was dried over $MgSO_4$ and the solvent was evaporated off. The residue was purified by chromatography ($CH_2Cl_2$/petroleum ether 6/4) Yield: 3.9 g=37% $^{13}C$ (100 MHz, $CDCl_3$) δ 150.96, 141.05, 133.29, 125.18, 119.73, 116.00, 66.85, 31.05, 25.20, 22.87

(b) 2-(Cyclohexyloxy)-aniline

Synthesis was carried out analogously to Example 1(b). $^{13}C$ (100 MHz, $CDCl_3$) δ 145.22, 137.62, 121.23, 118.28, 115.41, 114.12, 76.09, 32.13, 25.74, 23.84

(c) 2-(Cyclohexyloxy)-N-methylsulphonylanilide

Synthesis was carried out analogously to Example 1(c). The residue was recrystallised from ethanol. $^{13}C$ (100 MHz, $CDCl_3$) δ 147.59, 126.93, 125.45, 121.21, 121.10, 113.06, 76.63, 39.07, 31.92, 25.40, 23.87

(d) 3-(Cyclohexyloxy)-4-methylsulphonylaminobenzene-sulphonamide

Chlorosulphonic acid (0.15 ml, 2.26 mmol) was dissolved in chloroform (6 ml) and cooled to −25° C. At this temperature a solution of 2-(cyclohexyloxy)-N-methyl-sulphonylanilide (0.50 g, 1.85 mmol) in chloroform (5 ml) was slowly added dropwise. After 1 hour at −25° C. chlorosulphonic acid (0.15 ml, 2.26 mmol) was added dropwise again and stirring was continued for a further hour. Then phosphorus pentachloride (0.9 g, 4.5 mmol) was added and stirred for a further 2 hours at −20° C. It was poured onto ice water, the organic phase was separated off, dried over $MgSO_4$ and the solvent was evaporated off. The residue was used without further purification. Amidation to form the sulphonamide was carried out as described in Example 1(e). The crude product was purified by chromatography (silica gel, petroleum ether/ethyl acetate 4/6). Yield: 0.28 g=43% $^{13}C$ (100 MHz, DMSO-$d_6$) δ 152.94, 135.78, 126.47, 124.53, 123.37, 113.29, 75.89, 40.59, 31.04, 25.17, 23.22

EXAMPLE 11

3-(2-Chloro-4-bromophenoxy)-4-methylsulphonylamino-benzene-sulphonic acid-N-ethylamide

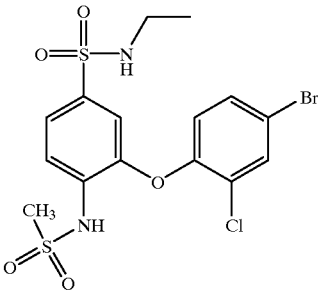

(a) 2-(2-Chloro-4-bromophenoxy)-nitrobenzene

Synthesis was carried out analogously to Example 1(a). The product could be used further without being purified. $^{13}C$ (100 MHz, $CDCl_3$) δ 150.59, 149.68, 140.91, 134.30, 133.66, 131.,32, 127.22, 126.03, 123.81, 122.07, 119.37, 117.87

(b) 2-(2-Chloro-4-bromophenoxy)-aniline

Synthesis was carried out analogously to Example 1(b). $^{13}C$ (100 MHz, $CDCl_3$) δ 152.34, 142.52, 138.31, 133.08, 130.85, 125.53, 125.30, 119.60, 119.22, 118.81, 116.71, 115.20

(c) 2-(2-Chloro-4-bromophenoxy)-N-methylsulphonylanilide

Synthesis was carried out analogously to Example 1(c). The product could be further processed without being purified. $^{13}C$ (100 MHz, $CDCl_3$) δ 150.21, 147.07, 133.71, 131.45, 127.34, 127.34, 125.84, 124.52, 122.48, 122.31, 117.94, 116.17, 39.73

(d) 3-(2-Chloro-4-bromophenoxy)-4-methylsulphonyl-aminobenzene sulphonic acid N-ethylamide Synthesis was carried out analogously to Examples 1(d) and 1(e). The product was purified by chromatography (silica gel, $CH_2Cl_2$/ethyl acetate 8/2) $^{13}C$ (100 MHz, DMSO-$d_6$) δ 150.35, 147.72, 137.18, 133.13, 132.14, 132.04, 126.55, 123.58, 123.35, 122.62, 117.34, 114.62, 41.00, 37.57, 14.73

EXAMPLE 12

3- (2-Bromo-4-chlorophenoxy) -4-methylsulphonylamino-benzene-sulphonic acid N-ethyl-amide

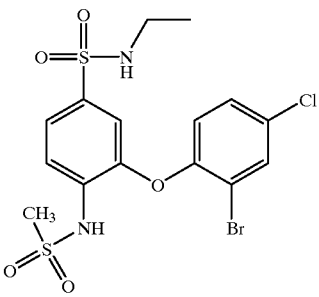

(a) 2-(2-Bromo-4-chlorophenoxy)-nitrobenzene

Synthesis was carried out analogously to Example 1 (a). The product could be used further without being purified $^{13}C$ (100 MHz, CDCl₃) δ 151.27, 149.74, 140.90, 134.28, 130.91, 129.04, 126.02, 123.77, 121.51, 119.43, 115.64

(b) 2-(2-Bromo-4-chlorophenoxy)-aniline

Synthesis was carried out analogously to Example 1(b). $^{13}$C (100 MHz, CDCl₃) δ 152.88, 142.63, 138.34, 133.13, 128.59, 128.45, 125.52, 119.69, 118.80, 118.51, 116.71, 113.66

(c) 2-(2-Bromo-4-chlorophenoxy)-N-methylsulphonylanilide

Synthesis was carried out analogously to Example 1(c). The product could be used further without being purified. $^{13}$C (100 MHz, CDCl₃) δ 150.87, 147.07, 133.74, 130.98, 129.17, 127.39, 125.82, 124.53, 122.28, 121.80, 116.32, 115.72,. 39.80

(d) 3-(2-Bromo-4-chlorophenoxy)-4-methylsulphonylamino-benzenesulphonic acid N-ethylamide Synthesis was carried out analogously to Examples 1(d) and 1(e). The product was purified by chromatography (silica gel, CH₂Cl₂/ethyl acetate 8/2) $^{13}$C (100 MHz, DMSO-d₆) δ 151.07, 147.92, 137.16, 133.20, 131.87, 129.81, 123.62, 123.02, 122.47, 120.20, 115.74, 114.48, 41.07, 37.57, 14.75

EXAMPLE 13

3-(3-Aminosulphonyl-5-chlorothienyl-2-thio)-4-methylsulphonylamino-benzenesulphonamide

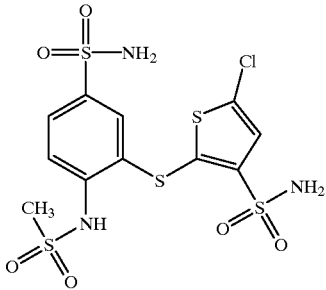

(a) 2-(Thienyl-2-thio)-nitrobenzene

Synthesis was carried out analogously to Example 1(a). The product was purified by chromatography (silica gel/ petroleum ether/ethyl acetate 4/6) $^{13}$C (100 MHz, CDCl₃) δ 144.90, 139.91, 138.40, 133.77, 133.38, 128.76, 128.71, 127.62, 125.64, 125.32

(b) 2-(5-Chlorothienyl-2-thio)-nitrobenzene 2-(Thienyl-2-thio)-nitrobenzene (7.77 g, 32.7 mmol) was dissolved in MeCN (50 ml) and heated to 60° C. under nitrogen. N-chlorosuccinimide (4.65 g, 35.0 mmol) was added quickly and the mixture was refluxed for 1 hour. The solvent was evaporated off in vacuo, the residue was dissolved in CH₂Cl₂, extracted twice with 4N NaOH and dried over MgSO₄. The solvent was evaporated off and the residue was used without any further purification. Yield: 8.56 g=85% $^{13}$C (100 MHz, CDCl₃) δ 144.94, 139.02, 138.37, 136.37, 133.96, 127.91, 127.53, 127.50, 125.76, 125.71

(c) 2-(5-Chlorothienyl-2-thio)-aniline

Synthesis was carried out analogously to Example 1(b). The product was further processed without being purified. $^{13}$C (100 MHz, CDCl₃) δ 147.42, 135.11, 131.40, 130.98, 130.75, 129.30, 126.61, 118.92, 115.65, 115.16

(d) 2-(5-Chlorothienyl-2-thio)-N-methylsulphonylanilide

Synthesis was carried out analogously to Example 1(c). The product was purified by chromatography (silica gel, CH₂Cl₂) $^{13}$C (100 MHz, CDCl₃) δ 136.86, 133.66, 133.60, 130.51, 130.31, 127.09, 126.14, 125.79, 125.36, 120.98, 39.79

(e) 3-(3-Aminosulphonyl-5-chlorothienyl-2-thio)-4-methylsulphonylaminobenzene-sulphonamide Synthesis was carried out analogously to Examples 1(d) and (e). The product was purified by crystallisation from CH₂Cl₂. $^{13}$C (100 MHz, DMSO-d₆) δ 141.92, 141.66, 141.07, 136.04, 131.89, 128.62, 128.21, 127.91, 127.38, 124.45, 41.09

EXAMPLE 14

3-(3,5-Dichlorothienyl-2-thio)-4-methylsulphonylamino-benzene-sulphonamide

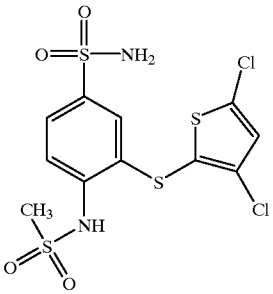

(a) 2-(Thienyl-2-thio)-nitrobenzene

Synthesis was carried out analogously to Example 1(a). The product was purified by chromatography (silica gel/ petroleum ether/ethyl acetate 4/6) $^{13}$C (100 MHz, CDCl₃) δ 144.90, 139.91, 138.40, 133.77, 133.38, 128.76, 128.71, 127.62, 125.64, 125.32

(b) 2-(3,5-Dichlorothienyl-2-thio)-nitrobenzene 2-(Thienyl-2-thio)-nitrobenzene (1.00 g, 3.68 mmol) was dissolved in MeCN (20 ml) and heated to 60° C. under nitrogen. N-chlorosuccinimide (4.91 g, 36.8 mmol) was added quickly and the mixture was refluxed for 4 hours. The solvent was evaporated off in vacuo, the residue was dissolved in CH₂Cl₂, extracted 4 times with 4N NaOH and dried over MgSO₄. The solvent was evaporated off and the residue was crystallised from CH₂Cl₂. Yield: 1.06 g=94% $^{13}$C (100 MHz, CDCl₃) δ 144.98, 136.73, 135.48, 134.60, 134.21, 128.18, 127.10, 126.08, 126.04, 121.93

(c) 2-(3,5-Dichlorothienyl-2-thio) -aniline

Synthesis was carried out analogously to Example 1(b). The product was further processed without being purified. $^{13}$C (100 MHz, CDCl₃) δ 147.85, 135.90, 131.23, 130.82, 128.18, 126.93, 126.58, 118.88, 116.17, 115.67

(d) 2- (3,5-Dichlorothienyl-2-thio) -N-methylsulphonyl-anilide

Synthesis was carried out analogously to Example 1(c). The product was crystallised from petroleum ether/ethyl acetate. $^{13}$C (100 MHz, CDCl₃) δ 137.43, 134.58, 133.16, 130.95, 130.09, 127.37, 125.68, 124.89, 124.40, 120.67, 39.86

(e) 2-(3,5-Dichlorothienyl-2-thio)-N-methylsulphonyl-aminobenzenesulphonamide

Synthesis was carried out analogously-to Examples 1(d) and (e). The product was purified by crystallisation from acetone/CH₂Cl₂. $^{13}$C (100 MHz, DMSO-d₆) δ 143.02, 137.26, 134.27, 133.14, 132.42, 128.84, 127.45, 125.29, 125.20, 122.76, 41.26

EXAMPLE 15

3-(2,4-Dimethyl-6-aminosulphonylphenoxy)-4-methylsulphonyl-aminobenzene-sulphonamide

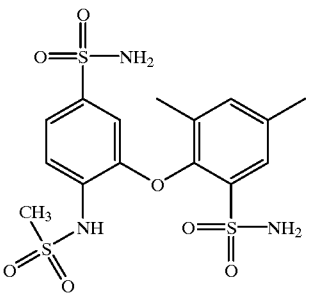

(a) 2-(2,4-Dimethylphenoxy)-nitrobenzene

Synthesis was carried out analogously to ExamDle 1(a). For purification the product was chromatographed (silica gel; $CH_2Cl_2$/petroleum ether 7/3). $^{13}C$ (100 MHz, $CDCl_3$) δ 151.61, 150.62, 140.85, 135.00, 133.94, 132.43, 129.84, 127.94, 125.72, 121.77, 120.05, 117.86, 20.74, 15.87

(b) 2- (2,4-Dimethylphenoxy) -aniline

Synthesis was carried out analogously to Example 1(b). $^{13}C$ (100 MHz, $CDCl_3$) δ 152.49, 144.77, 137.58, 132.88, 132.01, 128.72, 127.53, 123.47, 118.63, 118.06, 117.40, 116.09, 20.64, 16.01

(c) 2-(2,4-Dimethylphenoxy)-N-methylsulphonylanilide

Synthesis was carried out analogously to Example 1(c). The residue was recrystallised from ethanol. $^{13}C$ (100 MHz, $CDCl_3$) δ 150.79, 148.31, 134.77, 132.45, 129.51, 128.02, 126.91, 125.62, 123.01, 121.51, 119.73, 115.51, 39.43, 20.72, 15.96

(d) 3-(2,4-Dimethyl-6-aminosulphonylphenoxy)-4-methylsulphonylamino-benzenesulphonamide Synthesis was carried out analogously to Examples 1(d) and 1(e). The product was purified by chromatography (silica gel; $CH_2Cl_2$/ethyl acetate 3/2). $^{13}C$ (100 MHz, DMSO-$d_6$) δ 150.26, 148.71, 141.40, 141.03, 135.54, 134.06, 132.55, 130.87, 123.83, 120.79, 119.00, 112.97, 40.91, 19.16, 15.63

EXAMPLE 16

3-(5-Methyl-1,3,4-thiadiazolyl-2-thio)-4-methylsulphonylamino-benzenesulphonamide

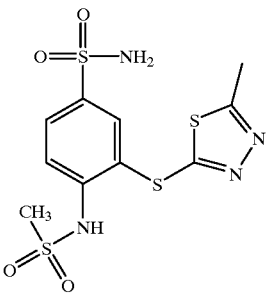

(a) 2-(5-Methyl-1,3,4-thiadiazolyl-2-thio)-nitrobenzene

Synthesis was carried out analogously to Example 1(a). For purification the product was chromatographed (silica gel; $CH_2Cl_2$). $^{13}C$ (100 MHz, $CDCl_3$) δ 170.57, 160.37, 146.09, 134.13, 133.29, 129.55, 127.37, 125.80, 16.08

(b) 2-(5-Methyl-1,3,4-thiadiazolyl-2-thio)-aniline

Synthesis was carried out analogously to Example 1(b). $^{13}C$ (100 MHz, $CDCl_3$) δ 168.84, 165.95, 149.03, 136.98, 132.74, 118.96, 115.99, 113.04, 15.65

(c) 2-(5-Methyl-1,3,4-thiadiazolyl-2-thio)-N-methylsulphonylanilide

Synthesis was carried out analogously to Example 1(c). The residue was recrystallised from $CH_2Cl_2$. $^{13}C$ (100 MHz, $CDCl_3$) δ 167.04, 164.39, 140.04, 136.97, 132.86, 125.52, 120.86, 119.96, 40.12; 15.76

(d) 3-(5-Methyl-1,3,4-thiadiazolyl-2-thio)-4-methylsulphonylaminobenzenesulphonamide Synthesis was carried out analogously to Examples 1(d) and 1(e). The product was recrystallised from $CH_2Cl_2$. $^{13}C$ (100 MHz, DMSO-$d_6$) δ 167.62, 164.43, 141.82, 141.45, 132.62, 128.54, 126.14, 124.93, 40.94, 15.49

EXAMPLE 17

3- (4-Chlorophenylthio) -4-methylsulphonylaminobenzenesulphonamide

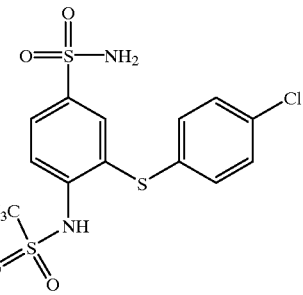

(a) 3-Chlorosulphanilamide

Sulphanilamide (50.0 g; 290.34 mmol) was dissolved in MeCN (500 ml) and heated to 60° C. N-chlorosuccinimide (40.06 g; 300 mmol) was quickly added and the mixture was refluxed for 2 hours. After cooling, the solvent was evaporated off, the residue was dissolved in ethyl acetate and extracted twice with 4N ammonia solution. The organic phase was washed with water, dried over $MgSO_4$ and evaporated down. It was recrystallised from ethyl acetate. Yield: 45 g=75% $^{13}C$ (100 MHz, DMSO-$d_6$) δ 147.87, 131.46, 127.22, 125.91, 115.84, 114.27

(b) 3-Chloro-4-nitrobenzenesulphonamide

3-Chlorosulphanilamide (2.27 g, 11 mmol) were dissolved in a mixture of glacial acetic acid (50 ml) and 35% hydrogen peroxide (18 ml) and heated to 70° C. After 3 hours the crystalline precipitate was filtered off and the filtrate was diluted with ethyl acetate. In order to destroy the excess peroxides, iron(II)sulphate was added and after filtering, the solvent was evaporated off. The residue was dissolved in ethyl acetate, washed with water, dried over $MgSO_4$ and concentrated by evaporation. Yield: 1.35 g=52% $^{13}C$ (100 MHz, DMSO-$d_6$) δ 149.26, 148.45, 128.72, 126.91, 125.98, 125.91

(c) 3-(4-Chlorophenylthio)-4-nitro-benzenesulphonamide

3-Chloro-4-nitrobenzenesulphonamide (1.08 g; 4.53 mmol), 4-chlorothiophenol (0.66 g; 4.53 mmol) and $K_2CO_3$ (0.64 g; 4.60 mmol) were refluxed in dioxan (30 ml) for 3 hours. The mixture was then diluted with $CH_2Cl_2$, filtered and washed with water. The organic phase was dried over $MgSO_4$ and evaporated down. The product was recrystallised from petroleum ether/ethyl acetate. Yield: 1.0 g=64% $^{13}C$ (100 MHz, DMSO-$d_6$) δ 148.57, 146.43, 138.07, 137.08, 135.76, 130.70, 128.74, 127.27, 125.43, 123.52

(d) 4-Amino-3-(4-chlorophenylthio)-benzenesulphonamide 3-(4-Chlorophenylthio)-4-nitro-benzenesulphonamide (0.50 g, 1.45 mmol), NH₄Cl (0.16 g; 2.90 mmol) and Fe powder (0.40 g; 7.25 mmol) were suspended in EtOH (10 ml)/water (5 ml) and refluxed for 30 minutes. The solution was filtered, evaporated down and the residue was taken up in CH₂Cl₂. It was washed with water, dried over MgSO₄ and evaporated down. The residue was used again in its crude form. Yield: 0.43 g=94% $^{13}$C (100 MHz, CDCl₃)d 152.17, 136.12, 133.59, 132.24, 130.75, 129.86, 129.38, 128.37, 114.69, 114.09

(e) 3-(4-Chlorophenylthio)-4-methylsulphonyl-amino-benzenesulphonamide

4-Amino-3-(4-chlorophenylthio)-benzenesulphonamide (0.43 g; 1.37 mmol) was dissolved in pyridine (10 ml) and at 0° C. methanesulphonic acid chloride (4.7 g; 41.0 mmol) was added dropwise. The solution came up to ambient temperature overnight, was then poured onto water and extracted with CH₂Cl₂. The solvent was evaporated off and the residue was stirred in dioxan (10 ml)/2N aqueous NaOH (10 ml). After acidifying with 2N HCl, the mixture was extracted with ethyl acetate, dried over MgSO₄ and evaporated down. The residue was recrystallised from CH₂Cl₂. Yield: 0.28 g=52% $^{13}$C (100 MHz, DMSO-d₆) δ 141.50, 140.23, 133.03, 132.82, 132.73, 129.79, 129.78, 129.46, 126.16, 123.90, 41.03

EXAMPLE 18

3-(N-Methylimidazolyl-2-thio)-4-methylsulphonylamino-benzenesulphonamide

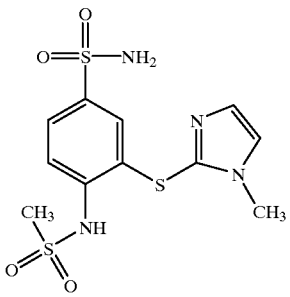

(a) 3-(N-Methylimidazolyl-2-thio)-4-nitro-benzenesulphonamide

Synthesis was carried out analogously to Example 17(c). The product was recrystallised from CH₂Cl₂. $^{13}$C (100 MHz, DMSO-d₆) δ 148.98, 145.94, 137.18, 133.80, 130.95, 127.69, 126.47, 124.49, 123.95, 33.64

(b) 3-(N-Methylimidazolyl-2-thio)-4-amino-benzenesulphonamide

Synthesis was carried out analogously to Example 17(d). The product was recrystallised from ethyl acetate. $^{13}$C (100 MHz, DMSO-d₆) δ 152.15, 136.60, 132.13, 131.33, 128.99, 128.01, 124.84, 114.40, 112.40, 33.66

(c) 3-(N-Methylimidazolyl-2-thio)-4-methylsulphonyl-amino-benzenesulphonamide

Synthesis was carried out analogously to Example 17(e). The product was recrystallised from CH₂Cl₂/MeOH. $^{13}$C (100 MHz, DMSO-d₆) δ 141.72, 139.05, 135.74, 131.13, 129.85, 127.15, 125.79, 125.70, 125.48, 41.19, 33.63

EXAMPLE 19

3-(Cyclohexylthio)-4-methylsulphonylaminobenzene-sulphonamide

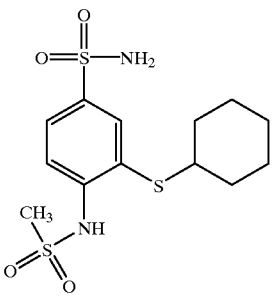

(a) 3-(Cyclohexylthio)-4-nitro-benzenesulphonamide

Synthesis was carried out analogously to Example 17(c). The product was recrystallised from diisopropylether. $^{13}$C (100 MHz, DMSO-d₆) δ 148.82, 148.10, 135.04, 126.68, 126.12, 122.87, 44.15, 32.07, 25.30, 25.18

(b) 3-(Cyclohexylthio)-4-amino-benzenesulphonamide

Synthesis was carried out analogously to Example 17(d). The product was recrystallised from diisopropylether. $^{13}$C (100 MHz, DMSO-d₆) δ 152.79, 135.75, 130.02, 128.49, 116.79, 113.84, 47.70, 33.61, 26.01, 25.61

(c) 3-(Cyclohexylthio)-4-methylsulphonylamino-benzenesulphonamide

Synthesis was carried out analogously to Example 17(e). $^{13}$C (100 MHz, CDCl₃) δ 143.35, 137.04, 134.83, 128.44, 123.18, 116.86, 49.57, 40.49, 33.41, 25.91, 25.35

EXAMPLE 20

3-(5-Trifluoromethylpyridyl-2-thio)-4-methylsulphonyl-amino-benzene-sulphonamide

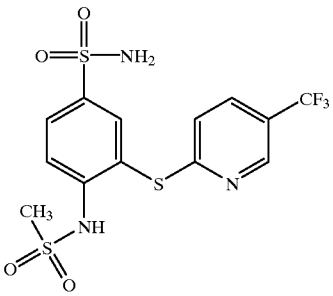

(a) 2-(5-Trifluoromethylpyridyl-2-thio)-nitrobenzene

Synthesis was carried out analogously to Example 1(a). For purification the residue was stirred with petroleum ether. $^{13}$C (100 MHz, CDCl₃) δ 161.90, 146.99, 146.96, 146.92, 146.88, 144.82, 135.05, 134.08, 134.05, 134.02, 133.99, 133.05, 129.14, 127.87, 125.37, 124.68, 124.38, 123.69, 122.00

(b) 2-(5-Trifluoromethylpyridyl-2-thio)-aniline

Synthesis was carried out analogously to Example 1(b). $^{13}$C (100 MHz, CDCl₃) δ 165.60, 149.24, 146.54, 146.49, 146.45, 146.40, 137.71, 133.60, 133.60, 133.57, 133.54, 133.50, 132.31, 129.26, 125.03, 122.90, 122.57, 122.32, 122.24, 119.35, 119.13, 115.69, 118.54, 111.41

(c) 2-(5-Trifluoromethylpyridyl-2-thio)-N-methyl-sulphonylanilide

Synthesis was carried out analogously to Example 1(c). The residue was purified by chromatography (silica gel;

CH$_2$Cl$_2$/ethyl acetate 19/1). $^{13}$C (100 MHz, CDCl$_3$) δ 163.03, 163.02, 146.90, 146.86, 146.81, 144.77, 140.46, 137.76, 134.17, 134.13, 134.10, 134.07, 132.53, 125.59, 124.68, 124.56, 124.23, 123.90, 123.57, 121.02, 120.87, 119.29, 40.02

(d) 3-(5-Trifluoromethylpyridyl-2-thio)-4-methylsulphonylaminobenzenesulphonamide Synthesis was carried out analogously to Examples 1(d) and 1(e). $^{13}$C (100 MHz, DMSO-d$_6$) δ 165.38, 146.27, 140.11, 137.79, 134.32, 131.63, 126.93, 125.67, 123.65, 121.88, 121.56, 120.80, 40.68

EXAMPLE 21

3-(4-Methoxyphenylthio)-4-methylsulphonylamino-benzenesulphonamide

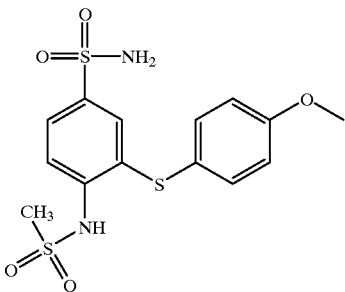

(a) 3-(4-Methoxyphenylthio)-4-nitro-benzenesulphonamide

Synthesis was carried out analogously to Example 17(c). The product was recrystallised from CH$_2$Cl$_2$. $^{13}$C (100 MHz, DMSO-d$_6$) δ 161.28, 148.48, 145.73, 140.12, 137.54, 127.21, 124.78, 122.89, 119.37, 116.31, 55.61

(b) 3-(4-Methoxyphenylthio)-4-amino-benzenesulphonamide

Synthesis was carried out analogously to Example 17(d). The product was recrystallised from CH$_2$Cl$_2$/petroleum ether. $^{13}$C (100 MHz, DMSO-d$_6$) δ 158.66, 152.24, 133.68, 131.23, 130.91, 128.14, 125.36, 115.16, 114.44, 113.92, 55.37

(c) 3-(4-Methoxyphenylthio)-4-methylsulphonylamino-benzenesulphonamide

Synthesis was carried out analogously to Example 17(e). The product was purified by chromatography (silica gel, CH$_2$Cl$_2$/MeOH 50/1) $^{13}$C (100 MHz, DMSO-d$_6$) δ 160.20, 142.05, 137.43, 135.63, 135.20, 126.53, 126.00, 124.48, 121.77, 115.82, 55.49, 41.44

EXAMPLE 22

3-(4-Methoxyphenylamino)-4-methylsulphonylamino-benzenesulphonamide

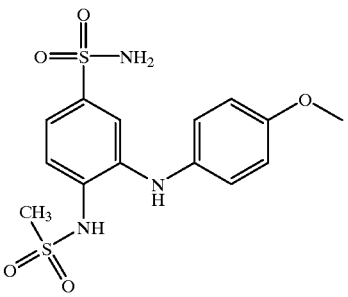

(a) 3-(4-Methoxyphenylamino)-4-nitro-benzenesulphonamide

Sodium hydride (1.69 g; 42.26 mmol) was suspended in absolute DMF and at 0° C. a solution of p-anisidine (5.20 g; 42.26 mmol) was added dropwise. After 30 minutes 3-chlorosulphanilamide (1.00 g; 4.23 mmol) was added and the mixture was stirred at 40° C. for 30 min. The mixture was poured onto water, adjusted to pH 1–2 with conc. hydrochloric acid and extracted with ethyl acetate. The combined organic phases were dried over MgSO$_4$. The residue was purified by chromatography (silica gel; CH$_2$Cl$_2$). $^{13}$C (100 MHz, DMSO-d$_6$) δ 157.83, 150.90, 137.80, 131.44, 130.66, 128.86, 125.82, 124.33, 115.13, 111.50, 55.56

(b) 3-(4-Methoxyphenylamino)-4-amino-benzenesulphonamide

Synthesis was carried out analogously to Example 1(b). The product was purified by chromatography (silica gel; CH$_2$Cl$_2$) $^{13}$C (100 MHz, DMSO-d$_6$) δ 154.36, 137.89, 137.22, 137.01, 120.11, 119.70, 119.60, 118.96, 117.04, 114.91, 55.72

(c) 3-(4-Methoxyphenylamino)-4-methylsulphonylamino-benzenesulphonamide

Synthesis was carried out analogously to Example 17(e). The product was purified by chromatography (silica gel; CH$_2$Cl$_2$/MeOH 10/1) $^{13}$C (100 MHz, DMSO-d$_6$) δ 154.99, 145.93, 134.76, 131.77, 130.93, 123.31, 122.21, 114.83, 114.07, 113.30, 55.37, 40.64

EXAMPLE 23

3-(2,4-Dimethylphenoxy)-4-methylsulphonylaminobenzene-sulphonamide

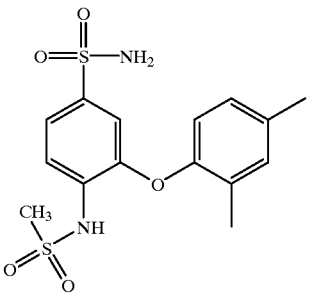

(a) 3-(2,4-Dimethylphenoxy)-4-nitro-benzenesulphonamide

Synthesis was carried out analogously to Example 17(c). The product was purified by chromatography (silica gel;

CH$_2$Cl$_2$/MeOH 25/1). $^{13}$C (100 MHz, DMSO-d$_6$) δ 150.41, 149.51, 149.01, 141.41, 135.57, 132.68, 129.34, 128.59, 126.70, 120.50, 119.75, 114.22, 20.46, 15.43

(b) 3-(2,4-Dimethylphenoxy)-4-aminobenzenesulphonamide

Synthesis was carried out analogously to Example 17(d). The product was recrystallised from CH$_2$Cl$_2$. $^{13}$C (100 MHz, DMSO-d$_6$) δ 151.64, 142.65, 133.16, 132.14, 130.59, 128.76, 127.85, 121.80, 118.94, 113.72, 113.55, 20.39, 15.74

(c) 3-(2,4-Dimethylphenoxy)-4-methylsulphonylaminobenzenesulphonamide

Synthesis was carried out analogously to Example 17(e). The product was purified by chromatography (silica gel, CH$_2$Cl$_2$/ethyl acetate 9/1) $^{13}$C (100 MHz, DMSO-d$_6$) δ 150.32, 149.63, 141.03, 134.57, 132.37, 130.39, 129.70, 128.30, 123.98, 120.54, 119.98, 112.30, 40.95, 20.47, 15.73

EXAMPLE 24

3-(Pyridyl-3-oxy)-4-methylsulphonylaminobenzene-sulphonamide

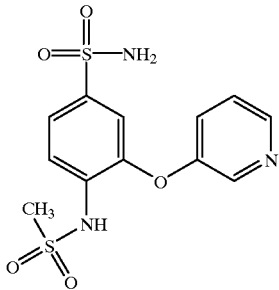

(a) 2-(Pyridyl-3-oxy)-nitrobenzene

Synthesis was carried out analogously to Example 1(a). The product was purified by chromatography (silica gel, ethyl acetate/petroleum ether 1:1) $^{13}$C NMR (100 MHz, CDCl$_3$) (152.91, 149.41, 145.48, 141.08, 134.48, 125.93, 125.59, 124.47, 124.31, 121.14.

(b) 2-(Pyridyl-3-oxy)-aniline

To a vigorously stirred suspension consisting of Rh/C and 2-(pyridyl-3-oxy)nitrobenzene in THF (25 mL) N$_2$H$_4$.H$_2$O was slowly added dropwise at 0° C. The reaction solution was left to come slowly to ambient temperature overnight. The reaction mixture was filtered and the filtrate was concentrated by evaporation. The residue thus formed was taken up in ethyl acetate (100 ml) and washed with dilute hydrochloric acid (3×50 ml, pH 2). The aqueous solution was neutralised (NaHCO$_3$) and extracted with CH$_2$Cl$_2$ (3×50 ml). The organic solution was dried over MgSO$_4$ and then evaporated down. The oil obtained was recrystallised from ethyl acetate. Yield: 5.60 g=64% $^{13}$C NMR (100 MHz, CDCl$_3$) (155.06, 143.83, 142.20, 140.20, 138.89, 125.66, 124.01, 123.58, 120.16, 118.76, 116.72.

(c) 2-(Pyridyl-3-oxy)-N-methylsulphonylanilide

Synthesis was carried out analogously to Example 1(c). The product was purified by chromatography (silica gel, CH$_2$Cl$_2$/MeOH 10:1) $^{13}$C NMR (100 MHz, CDCl$_3$) (152.66, 146.54, 145.51, 141.26, 128.44, 125.72, 125.67, 125.09, 124.37, 121.71, 118.09, 39.84.

(d) 3-(Pyridyl-3-oxy)-4-methylsulphonylaminobenzene-sulphonamide

Synthesis was carried out analogously to Examples 1(d) and 1(e). The residue was digested with diisopropylether and recrystallised from ethanol. $^{13}$C (100 MHz, DMSO-d$_6$) (152.50, 147.68, 145.42, 141.42, 140.90, 132.30, 126.37, 124.92, 123.68, 121.97, 115.81, 40.94.

EXAMPLE 25

3-(2-Chlorophenylthio)-4-methylsulphonylaminobenzene-sulphonamide

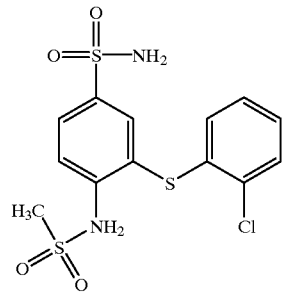

(a) 3-(2-Chlorophenylthio)-4-nitro-benzenesulphonamide

Synthesis was carried out analogously to Example 17(c). The product was recrystallised from petroleum ether/CH$_2$Cl$_2$. $^{13}$C (100 MHz, DMSO-d$_6$) δ 148.74, 146.51, 138.38, 137.96, 136.51, 133.00, 131.19, 129.24, 128.43, 127.50, 124.99, 123.75

(b) 3-(2-Chlorophenylthio)-4-amino-benzenesulphonamide

Synthesis was carried out analogously to Example 17 (d). The product was recrystallised from CH$_2$Cl$_2$. $^{13}$C (100 MHz, DMSO-d$_6$) δ 153.62, 135.57, 134.97, 131.54, 130.27, 129.79, 129.52, 127.90, 126.92, 126.22, 114.42, 108.95

(c) 3-(2-Chlorophenylthio)-4-methylsulphonylaminobenzenesuiphonamide

Synthesis was carried out analogously to Example 17(e). The product was purified by chromatography (silica gel, CH$_2$Cl$_2$/MeOH 19/1) and recrystallised from CHCl$_3$. $^{13}$C (100 MHz, DMSO-d$_6$) δ 141.48, 141.08, 133.36, 133.28, 131.23, 130.80, 130.28, 129.17, 128.45, 127.60, 126.99, 124.62, 41.22

EXAMPLE 26

3-(4-Bromophenylthio)-4-methylsulphonylaminobenzenesulphonamide

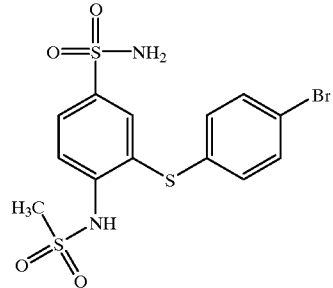

(a) 3-(4-Bromophenylthio)-4-nitro-benzenesulphonamide

Synthesis was carried out analogously to Example 17(c). The product was recrystallised from petroleum ether/CH$_2$Cl$_2$. $^{13}$C (100 MHz, DMSO-d$_6$) δ 148.56, 146.50, 137.85, 137.19, 133.62, 129.27, 127.26, 125.50, 124.49, 123.56

(b) 3-(4-Bromophenylthio)-4-amino-benzenesulphonamide

Synthesis was carried out analogously to Example 17(d). $^{13}$C (100 MHz, CDCl$_3$)d 153.16, 135.54, 135.18, 132.08, 131.34, 129.20, 128.72, 118.83, 114.28, 110.70

(c) 3-(4-Bromophenylthio)-4-methylsulphonylamino-benzenesulphonamide

Synthesis was carried out analogously to Example 17(e). The product was purified by chromatography (silica gel, petroleum ether/ethyl acetate 1/1). $^{13}$C (100 MHz, DMSO-d$_6$) δ 141.75, 139.98, 133.44, 132.79, 132.75, 130.11, 130.05, 126.41, 125.04, 121.25, 41.21

EXAMPLE 27

3-(4-Trifluoromethoxyphenylthio)-4-methylsulphonyl-aminobenzene-sulphonamide

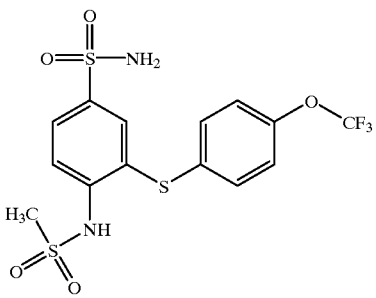

$^{13}$C (100 MHz, DMSO-d$_6$) δ 141.70, 141.53, 141.06, 132.48, 128.91, 127.72, 127.42, 127.10, 126.47, 126.40, 126.36, 124.38, 41.10

EXAMPLE 28

3-(Furyl-2-thio)-4-methylsulphonyl-aminobenzenesulphonamide

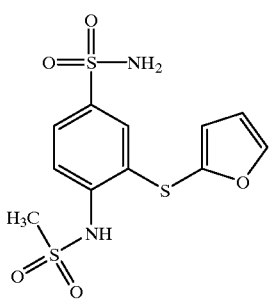

EXAMPLE 29

3-(3-Chlorophenylthio)-4-methylsulphonyl-aminobenzenesulphonamide

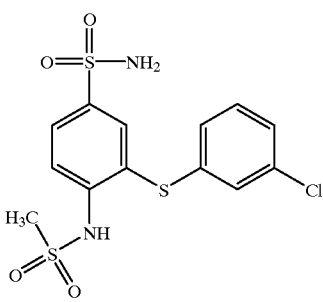

(a) 3-(3-Chlorophenylthio)-4-nitro-benzenesulphonamide

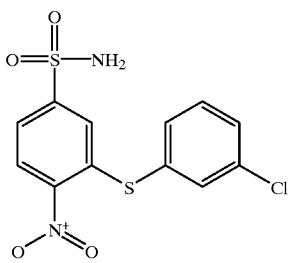

Synthesis was carried out analogously to Example 14(c). The product was recrystallised from petroleum ether/CH$_2$Cl$_2$. $^{13}$C (100 MHz, DMSO-d$_6$) δ 148.58, 146.62, 137.58, 134.73, 134.37, 133.85, 132.22, 132.12, 130.70, 127.23, 125.74, 123.70

(b) 3-(3-Chlorophenylthio)-4-amino-benzenesulphonamide

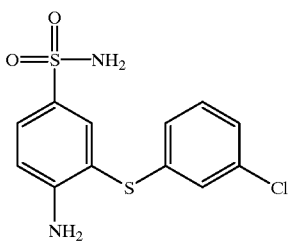

Synthesis was carried out analogously to Example 14(d). The product was recrystallised from CHCl$_3$. $^{13}$C (100 MHz, DMSO-d$_6$) δ 153.32, 138.54, 135.44, 133.87, 131.36, 130.92, 129.43, 125.83, 125.71, 125.16, 114.33, 110.09

(c) 3-(3-Chlorophenylthio)-4-methylsulphonylamino-benzenesulphonamide

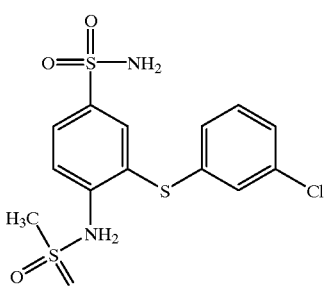

Synthesis was carried out analogously to Example 14(e). The product was purified by chromatography (silica gel, CH$_2$Cl$_2$/MeOH 19/1) $^{13}$C (100 MHz, DMSO-d$_6$) δ 141.62, 140.60, 136.64, 134.16, 131.42, 131.05, 129.46, 128.80, 128.74, 127.72, 126.93, 124.73, 41.19

EXAMPLE 30

3-(2,4,6-Trichlorophenylthio)-4-methylsulphonylaminobenzene-sulphonamide

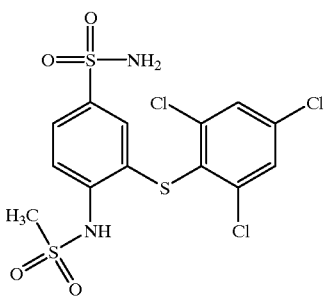

$^{13}$C (100 MHz, DMSO-d$_6$) δ 143.01, 141.54, 137.05, 136.34, 134.17, 129.56, 129.34, 128.76, 127.84, 126.39, 124.43, 123.00, 41.49

EXAMPLE 31

3-(4-Trifluoromethylphenylthio)-4-methylsulphonylaminobenzene-sulphonamide

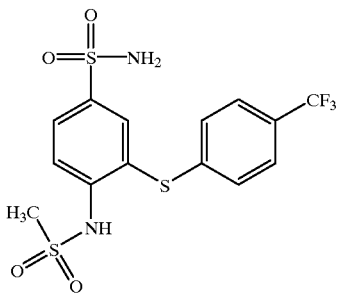

EXAMPLE 32

3-(Phenylthio)-4-methylsulphonylamino-benzenesulphonamide

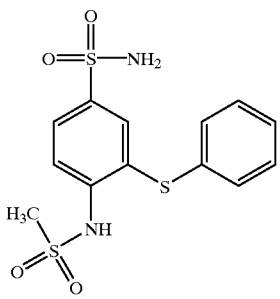

EXAMPLE 33

3-(2-Bromo-4-chlorophenylthio)-4-methylsulphonylaminobenzenesulphonamide

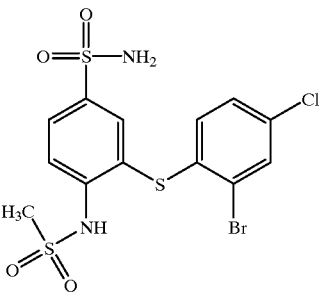

EXAMPLE 34

3-(2,5-Dichlorophenylthio)-4-methyl-sulphonylaminobenzenesulphonamide

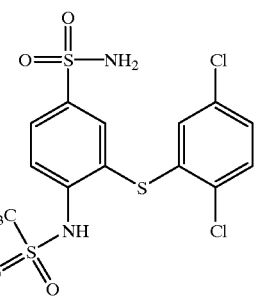

$^{13}$C (100 MHz, DMSO-d$_6$)d 141.76, 141.64, 136.21, 132.70, 131.96, 131.60, 131.28, 129.08, 128.54, 127.85, 125.95, 124.81, 41.29

EXAMPLE 35

3-(2,3-Dichlorophenylthio)-4-methylsulphonylaminobenzenesulphonamide

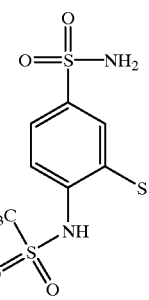

$^{13}$C (100 MHz, DMSO-d$_6$) δ 142.07, 141.49, 137.28, 132.70, 132.57, 129.74, 128.99, 128.65, 128.02, 127.84, 125.37, 124.24, 41.19

EXAMPLE 36

3-(2,4-Dichlorophenoxy)-4-methylsulphonylamino-benzenesulphonic acid N-methylamide

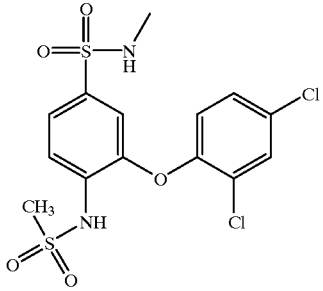

3-(2,4-Dichlorophenoxy)4-methylsulphonylaminobenzene-sulphonic acid chloride N-methylamide (HN-56203) 3-(2,4-dichlorophenoxy)-4-methylsulphonylaminobenzenesulphonic acid chloride (0.56 g, 1.3 mmol) was dissolved in dioxan (15 ml) and at 0° C. it was added dropwise to a solution of methylamine hydrochloride (1.18 g, 17 mmol) in 1N aqueous NaOH (15 ml, 15 mmol) and dioxan (20 ml). The mixture was stirred for 1 hour at 0° C., acidified with 1N HCl and extracted with ethyl acetate. The combined organic phases were dried over $MgSO_4$ and the solvent was evaporated off. The residue was purified by chromatography (silica gel, $CH_2Cl_2$/ethyl acetate 9/1). Yield: 0.25 g=45% $^{13}$C (100 MHz, $CDCl_3$) δ 148.35, 146.21, 134.97, 132.03, 131.28, 131.16, 128.98, 127.15, 123.15, 123.12, 119.56, 113.81, 40.45, 29.18

EXAMPLE 37

3-(2,4-Dichlorophenoxy)-4-methylsulphonylaminobenzene-sulphonic acid N,N-dimethylamide

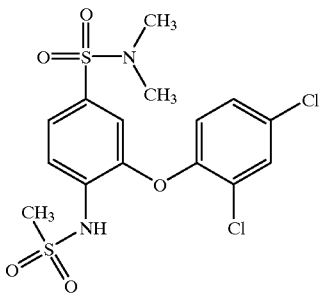

3-(2,4-Dichlorophenoxy)-4-methylsulphonylaminobenzene-sulphonic acid chloride (1.12 g, 2.6 mmol) was dissolved in dioxan (5 ml) and at 0° C. added dropwise to a solution of dimethylamine hydrochloride (1.10 g, 13.4 mmol) in 1N aqueous NaOH (13 ml, 13 mmol) and dioxan (13 ml). The mixture was stirred for 1 hour at 0° C., acidified with 1N HCl and extracted with ethyl acetate. The combined organic phases were dried over $MgSO_4$ and the solvent was evaporated off. The residue was purified by chromatography (silica gel, petroleum ether/ethyl acetate 6/4). Yield: 0.27 g=24% $^{13}$C (100 MHz, DMSO-$d_6$) δ 150.02, 147.24, 133.01, 130.81, 130.42, 129.53, 129.18, 126.03, 123.74, 123.17, 122.57, 115.72, 41.03, 37.59

EXAMPLE 38

3-(2,4-Dichlorophenoxy)-4-methylsulphonylaminobenzene-sulphonic acid azetidinium amide

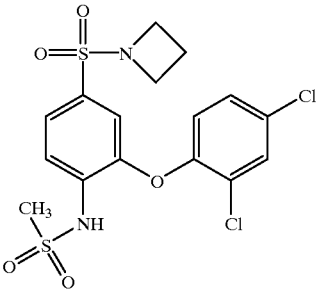

3-(2,4-Dichlorophenoxy)-4-methylsulphonylaminobenzene-sulphonic acid chloride (0.51 g, 1.2 mmol) was dissolved in dioxan (5 ml) and at 0° C. added dropwise to a solution of azetidinium tetrafluoroborate (1.48 g, 10.2 mmol) in 1N aqueous NaOH (10 ml, 10 mmol) and dioxan (20 ml). The mixture was stirred for 1 hour at 0° C., acidified with 1N HCl and extracted with ethyl acetate. The combined organic phases were dried over $MgSO_4$ and the solvent was evaporated off. The residue was purified by chromatography (silica gel, $CH_2Cl_2$/ethyl acetate 9/1) Yield: 0.18 g=33% $^{13}$C (100 MHz, DMSO-$d_6$) δ 149.94, 147.28, 133.32, 130.49, 129.70, 129.58, 129.26, 126.15, 124.39, 122.87, 122.86, 116.02, 50.94, 41.08, 14.87

EXAMPLE 39

3-(2,4-Dichlorophenoxy)-4-methylsulphonyl-aminobenzenesulphonic acid N-ethylamide

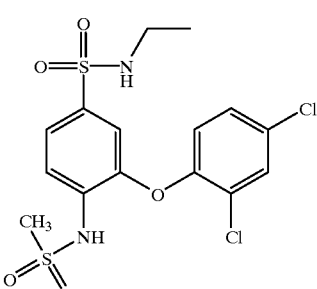

3-(2,4-Dichlorophenoxy)-4-methylsulphonylaminobenzene-sulphonic acid chloride (1.64 g, 3.8 mmol) was dissolved in dioxan (5 ml) and at 0° C. added dropwise to a solution of ethylamine hydrochloride (2.51 g, 30.8 mmol) in 1N aqueous NaOH (30 ml, 30 mmol) and dioxan (30 ml). The mixture was stirred for 1 hour at 0° C., acidified with 1N HCl and extracted with ethyl acetate. The combined organic phases were dried over $MgSO_4$ and the solvent was evaporated off. The residue was purified by chromatography (silica gel, $CH_2Cl_2$/ethyl acetate 10/0.5). Yield: 0.46 g=28% $^{13}$C (100 MHz, DMSO-$d_6$) δ 149.88, 147.82, 137.13, 131.96, 130.44, 129.66, 129.24, 126.31, 123.58, 123.03, 122.58, 114.53, 41.00, 37.57, 14.73

EXAMPLE 40

3-(2,4-Dichlorophenoxy)-4-methylsulphonylaminobenzene-sulphonic acid N,N-diethyl-amide

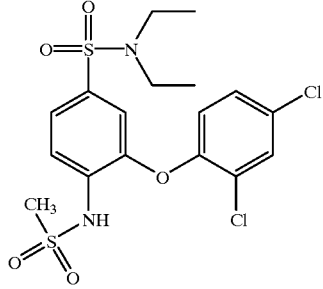

3-(2,4-Dichlorophenoxy)-4-methylsulphonylaminobenzene-sulphonic acid chloride (1.08 g, 2.50 mmol) was dissolved in dichloromethane (5 ml) and at 0° C. added dropwise to a solution of diethylamine (0.30 ml, 2.51 mmol) in pyridine (20 ml). The mixture was stirred for 1 hour at 0° C., acidified with 1N HCl and extracted with ethyl acetate. The combined organic phases were dried over MgSO$_4$ and the solvent was evaporated off. The residue was purified by chromatography (silica gel, CH$_2$Cl$_2$). Yield: 0.22 g=19% $^{13}$C (100 MHz, DMSO-d$_6$) δ 149.98, 147.50, 136.21, 132.37, 130.43, 129.63, 129.21, 126.15, 123.56, 122.86, 122.72, 114.90, 41.77, 41.02, 14.02

EXAMPLE 41

3-(2,4-Dichlorophenoxy)-4-methylsulphonylaminobenzene-sulphonic acid morpholinamide

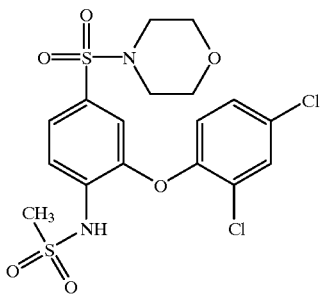

3-(2,4-Dichlorophenoxy)-4-methylsulphonylaminobenzene-sulphonic acid chloride (1.36 g, 3.2 mmol) was dissolved in dioxan (5 ml) and at 0° C. added dropwise to a solution of morpholine (2.25 ml, 25.6 mmol) in 1N aqueous NaOH (26 ml, 26 mmol) and dioxan (20 ml). The mixture was stirred for 1 hour at 0° C., acidified with 1N HCl and extracted with ethyl acetate. The combined organic phases were dried over MgSO$_4$ and the solvent was evaporated off. The residue was purified by chromatography (silica gel, CH$_2$Cl$_2$/ethyl acetate 9/1). Yield: 0.93 g=60% $^{13}$C (100 MHz, DMSO-d$_6$) δ 150.02, 147.15, 133.44, 130.43, 129.51, 129.31, 129.18, 126.23, .125.98, 123.95, 123.02, 122.51, 116.78, 115.83, 65.41, 45.83, 41.03

EXAMPLE 42

3-(2,4-Dichlorophenoxy)-4-methylsulphonyl-aminobenzenesulphonic acid hydroxyamide

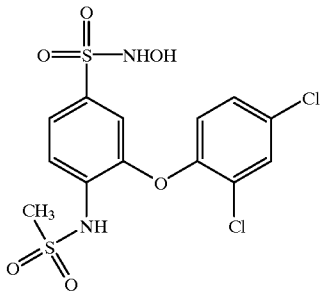

3-(2,4-Dichlorophenoxy)-4-methylsulphonylaminobenzene-sulphonic acid chloride (0.17 g, 0.40 mmol) was dissolved in dioxan (3 ml) and added dropwise at 0° C. to a solution of hydroxylamine hydrochloride (0.28 g, 4.0 mmol) and sodium carbonate (0.43 g, 4.0 mmol) in water (5 ml) and dioxan (2 ml). The mixture was stirred for 2 hours at 0° C., acidified with conc. HCl and extracted with ethyl acetate. The combined organic phases were dried over MgSO$_4$ and the solvent was evaporated off. The residue was purified by chromatography (silica gel, chloroform/MeOH 9/1). Yield: 0.1 g=62% $^{13}$C (100 MHz, DMSO-d$_6$) δ 149.92, 147.35, 133.60, 132.91, 130.40, 129.60, 129.20, 126.25, 124.41, 122.99, 122.90, 116.22, 41.09

EXAMPLE 43

3-(2,4-Dichlorophenoxy)-4-methylsulphonyl-aminobenzenesulphonic acid O-methylhydroxyamide

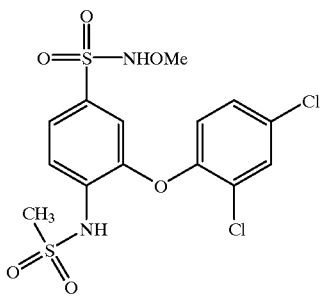

3-(2,4-Dichlorophenoxy)-4-methylsulphonylaminobenzene-sulphonic acid chloride (1.1 g, 2.55 mmol) was dissolved in CH$_2$Cl$_2$ (5 ml) and at 0° C. added dropwise to a solution of O-methylhydroxylamine hydrochloride (0.3 g, 3.6 mmol) and DMAP (0.44 g, 3.6 mmol) in pyridine (20 ml). The mixture was stirred at 0° C. for 2 hours and then evaporated down. The residue was dried in vacuo and purified by chromatography (silica gel, chloroform/MeOH 50/1). Yield: 0.28 g=25% $^{13}$C (100 MHz, DMSO-d$_6$) δ 149.89, 147.25, 133.47, 133.06, 130.42, 129.64, 129.20, 126.24, 124.42, 122.85, 122.71, 116.00, 64.44, 41.11

EXAMPLE 44

3-(2,4-Dichlorophenoxy)-4-methylsulphonyl-aminobenzenesulphonic acid N,O-dimethyl-hydroxyamide

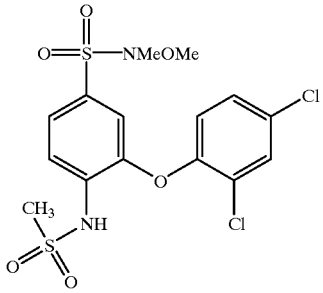

3-(2,4-Dichlorophenoxy)-4-methylsulphonylaminobenzene-sulphonic acid chloride (1.1 g, 2.55 mmol) was dissolved in CH$_2$Cl$_2$ (5 ml) and at 0° C. added dropwise to a solution of N,O-dimethylhydroxylamine hydrochloride (0.34 g, 3.5 mmol) and DMAP (0.44 g, 3.6 mmol) in pyridine (20 ml). The mixture was stirred for 2 hours at 0° C. and then evaporated down. The residue was dried in vacuo and purified by chromatography (silica gel, CH$_2$Cl$_2$). Yield: 0.43 g=37% $^{13}$C (100 MHz, DMSO-d$_6$) δ 149.94, 146.71, 134.37, 130.45, 129.64, 129.18, 126.97, 126.10, 125.77, 122.77, 122.20, 117.43, 63.36, 41.12, 38.97

EXAMPLE 45

3-(2,4-Dichlorophenoxy)-4-methylsulphonylaminobenzene-sulphonic acid N-benzylamide

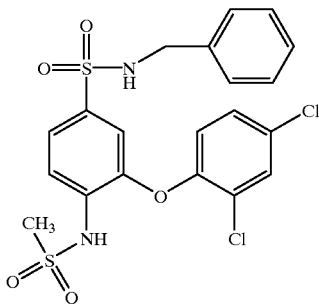

3-(2,4-Dichlorophenoxy)-4-methylsulphonylaminobenzene-sulphonic acid chloride (1.08 g, 2.51 mmol) was dissolved in CH$_2$Cl$_2$ (5 ml) and at 0° C. added dropwise to a solution of benzylamine (0.35 ml, 3.2 mmol) in pyridine (20 ml). The mixture was stirred for 2 hours at 0° C. and then evaporated down. The residue was dried in vacuo and purified by chromatography (silica gel, CHCl$_3$/MeOH 19/1). Yield: 0.18 g=15% $^{13}$C (100 MHz, DMSO-d$_6$) δ 149.94, 147.70, 137.38, 137.26, 132.04, 130.41, 129.55, 129.19, 128.30, 127.71, 127.28, 126.23, 123.52, 122.87, 122.67, 114.71, 46.23, 40.92

EXAMPLE 46

3-(2,4-Dichlorophenoxy)-4-methylsulphonyl-aminobenzenesulphonic acid 4-(methoxyphenyl) amide

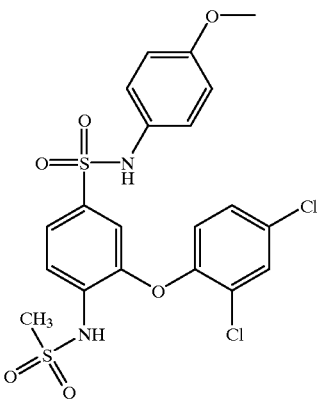

3-(2,4-Dichlorophenoxy)-4-methylsulphonylaminobenzene-sulphonic acid chloride (1.08 g, 2.51 mmol) was dissolved in CH$_2$Cl$_2$ (5 ml) and at 0° C. added dropwise to a solution of p-anisidine (0.46 g, 3.7 mmol) in pyridine (20 ml). The mixture was stirred at 0° C. for 1 hour and evaporated down. The residue was dried in vacuo and purified by chromatography (silica gel, CH2$_{Cl2}$/ethyl acetate 19/1). Yield: 0.37 g=29% $^{13}$C (100 MHz, DMSO-d$_6$) δ 156.96, 149.63, 147.53, 135.54, 132.26, 130.44, 129.82, 129.77, 129.13, 126.41, 124.11, 123.12, 123.07, 122.72, 114.57, 114.42, 55.31, 41.03

EXAMPLE 47

3-(2,4-Dichlorophenoxy)-4-methylsulphonyl-aminobenzenesulphonic acid-(2-pyridyl)-amide

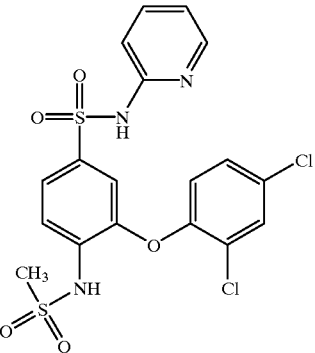

3-(2,4-Dichlorophenoxy)-4-methylsulphonylaminobenzene-sulphonic acid chloride (1.08 g, 2.51 mmol) was dissolved in CH$_2$Cl$_2$ (5 ml) and at 0° C. added dropwise to a solution of 2-aminopyridine (0.30 g, 3.2 mmol) in pyridine (20 ml). The mixture was stirred for 1 hour at 0° C. and then evaporated down. The residue was dried in vacuo and purified by chromatography (silica gel, chloroform/MeOH 19/1). Yield: 0.22 g=18% $^{13}$C (100 MHz, DMSO-d$_6$) (155.91, 150.50, 148.60, 146.84, 141.94, 139.86, 130.21, 129.08, 128.95, 127.90, 126.19, 125.43, 123.47, 121.39, 114.14, 112.17, 111.81, 40.66

EXAMPLE 48

3-(2,4-Dichlorophenoxy)-4-methylsulphonyl-aminobenzenesulphonic acid (3-pyridyl)-amide

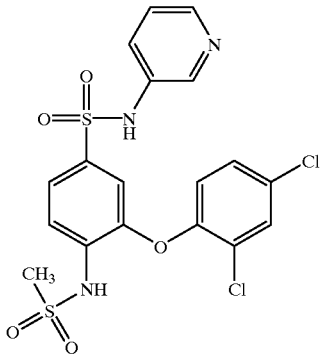

3-(2,4-Dichlorophenoxy)-4-methylsulphonylaminobenzene-sulphonic acid chloride (1.08 g, 2.51 mmol) was dissolved in $CH_2Cl_2$ (5 ml) and at 0° C. added dropwise to a solution of 3-aminopyridine (0.30 g, 3.2 mmol) in pyridine (20 ml). The mixture was stirred for 1 hour at 0° C. and then evaporated down. The residue was dried in vacuo and purified by chromatography (silica gel, chloroform/MeOH 19/1). Yield: 0.18 g=15% $^{13}C$ (100 MHz, DMSO-$d_6$) (149.43, 147.65, 145.75, 142.35, 134.92, 134.17, 132.57, 130.56, 130.03, 129.30, 128.21, 126.52, 124.12, 123.39, 122.90, 122.70, 114.05, 41.07

EXAMPLE 49

[3-(2,4-Dichlorophenoxy)-4-methylsulphonylamino-phenylsulphamoyl]-β-alanine

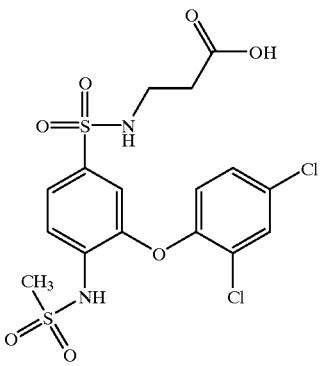

3-(2,4-Dichlorophenoxy)-4-methylsulphonylamino-benzenesulphonic acid chloride (2.28 g, 5.3 mmol) was dissolved in dioxan (5 ml) and at 0° C. added dropwise to a solution of b-alanine (3.77 g, 42.4 mmol) in 1N aqueous NaOH (42 ml, 42 mmol) and dioxan (20 ml). The mixture was stirred for 3 hours at 0° C., acidified with conc. HCl and extracted with ethyl acetate The combined organic phases were dried over $MgSO_4$ and the solvent was evaporated off. The residue was purified by chromatography (silica gel, petroleum ether/ethyl acetate/HOAc 1/1/0.1). Yield: 0.52 g=20% $^{13}C$ (100 MHz, DMSO-$d_6$) δ 172.25, 150.01, 147.65, 136.43, 132.52, 130.41, 129.48, 129.18, 126.14, 123.38, 122.81, 122.78, 114.83, 40.97, 38.62, 34.20

EXAMPLE 50

3-(2,4-Dichlorophenoxy)-4-methylsulphonyl-aminobenzenesulphonic acid 2-hydroxy-ethylamide

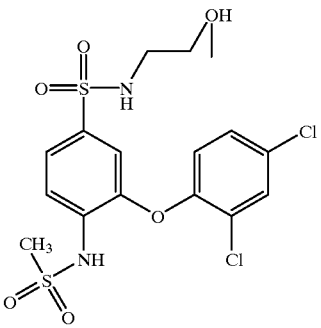

3-(2,4-Dichlorophenoxy)-4-methylsulphonylamino-benzenesulphonic acid chloride (1.1 g, 2.5 mmol) was dissolved in $CH_2Cl_2$ (5 ml) and at 0° C. added dropwise to a solution of ethanolamine (0.20 g, 3.3 mmol) in pyridine (20 ml). The mixture was stirred for 1 hour at 0° C. and then evaporated down. The residue was dried in vacuo and purified by chromatography (silica gel, chloroform/MeOH 19/1). Yield: 0.28 g=24% $^{13}C$ (100 MHz, DMSO-$d_6$) δ 149.97, 147.71, 137.12, 130.41, 129.53, 129.20, 126.19, 123.55, 123.52, 122.83, 122.66, 114.77, 59.95, 45.11, 41.01

EXAMPLE 51

3-(2,4-Dichlorophenoxy)-4-methylsulphonylaminobenzene-sulphonic acid bis(hydroxymethyl)methylamide

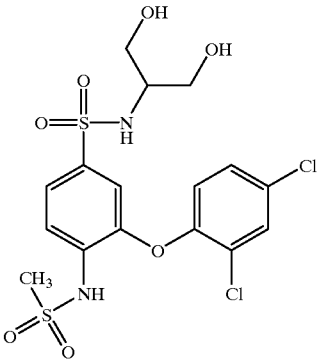

3-(2,4-Dichlorophenoxy)-4-methylsulphonylaminobenzene-sulphonic acid chloride (1.8 g, 2.51 mmol) was dissolved in $CH_2Cl_2$ (5 ml) and at 0° C. added dropwise to a solution of bis(hydroxymethyl)methylamine (0.44 g, 4.8 mmol) in pyridine (20 ml). The mixture was stirred for 2 hours at 0° C. and then evaporated down. The residue was dried in vacuo and purified by chromatography (silica gel, chloroform/MeOH 19/1) Yield: 0.35 g=29% $^{13}C$ (100 MHz, DMSO-$d_6$) δ 150.17, 147.50, 138.39, 132.09, 130.34, 129.29, 129.10, 126.02, 123.25, 122.75, 122.51, 115.22, 60.36, 57.07, 40.94

EXAMPLE 52

4-[3-(2,4-Dichlorophenoxy)-4-methylsulphonylamino-phenylsulphamoyl]-E-cinnamic acid

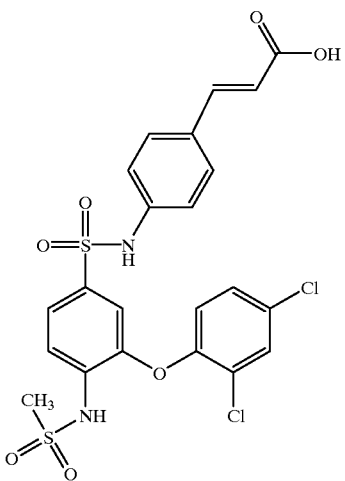

3-(2,4-Dichlorophenoxy)-4-methylsulphonylaminobenzene-sulphonic acid chloride (1.1 g, 2.55 mmol) was dissolved in CH$_2$Cl$_2$ (5 ml) and at 0° C. added dropwise to a solution of 4-aminocinnamic acid hydrochloride (0.65 g, 43.3 mmol) and DMAP (0.44 g, 3.6 mmol) in pyridine (20 ml). The mixture was stirred for 7 hours at 0° C. and then evaporated down. The residue was dried in vacuo and purified by chromatography (silica gel, petroleum ether/ethyl acetate/HOAc 1/1/0.1). Yield: 0.43 g=30% $^{13}$C (100 MHz, DMSO-d$_6$) δ 167.68, 149.54, 147.56, 143.23, 139.25, 130.47, 130.33, 130.07, 129.89, 129.42, 129.21, 126.45, 123.19, 122.96, 122.71, 120.18, 118.42, 114.28, 113.74, 41.10

EXAMPLE 53

3-(2,4-Dichlorophenoxy)-4-methylsulphonyl-aminophenylsulphonic acid N-methylsulphonylamide

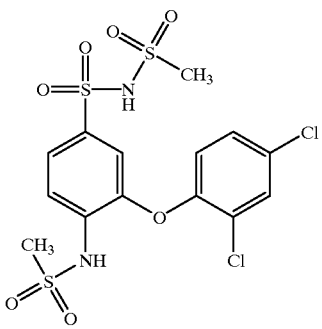

Methanesulphonamide (1.2 g, 12.5 mmol) was dissolved in absolute THF (50 ml) and TMEDA (7.55 ml) was added. The solution was cooled to –50° C. and BuLi (7.8 ml, 12.5 mmol) was added. The mixture was stirred at this temperature for 15 minutes, then a solution of 3-(2,4-dichlorophenoxy)-4-methylsulphonylaminobenzenesulphonic acid chloride (0.5 g, 1.25 mmol) in THF (5 ml) was added dropwise. The mixture was stirred for 4 hours at –40° C. and quenched by the addition of acetic acid. The mixture was dissolved in ethyl acetate and extracted with water. The combined organic phases were dried over MgSO$_4$ and the solvent was evaporated off. The residue was purified by chromatography (silica gel, CHCl$_3$/MeOH 18/3). Yield: 0.18 g=29% $^{13}$C (100 MHz, DMSO-d$_6$) δ 150.59, 147.38, 144.52, 130.19, 129.82, 128.93, 128.80, 125.72, 124.30, 122.50, 121.96, 115.67, 42.92, 40.84

EXAMPLE 54

3-(2,4-Dichlorophenoxy)-4-methylsulphonyl-aminophenylsulphonic acid N-formylamide

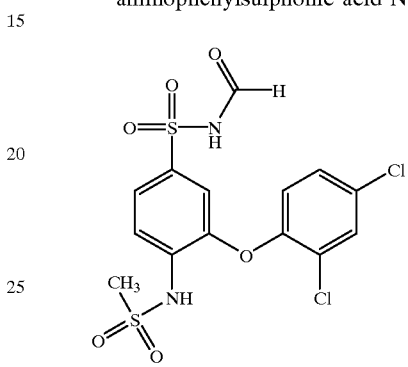

Formamide (0.5 ml, 12.5 mmol) was dissolved in absolute THF (50 ml) and TMEDA (7.55 ml) was added. The solution was cooled to –50° C. and BuLi (7.8 ml, 12.5 mmol) was added. The mixture was stirred for 15 minutes at this temperature, then a solution of 3-(2,4-dichlorophenoxy)-4-methylsulphonylaminobenzenesulphonic acid chloride (0.5 g, 1.25 mmol) in THF (5 ml) was added dropwise. The mixture was stirred for 5 hours at –40° C. and quenched by the addition of acetic acid. The mixture was dissolved in ethyl acetate and extracted with water. The combined organic phases were dried over MgSO$_4$ and the solvent was evaporated off. The residue was purified by chromatography (silica gel, CHCl$_3$/MeOH 9/2). Yield: 0.04 g=7% $^{13}$C (100 MHz, MeOH-d$_4$) δ 166.05, 150.96, 149.39, 139.60, 133.78, 132.83, 132.16, 130.45, 128.84, 125.06, 123.82, 123.57, 115.15, 41.10

EXAMPLE 55

3-(2,4-Dichlorophenoxy)-4-methylsulphonyl-aminophenylsulphonic acid N-(N'-formyl)hydrazide

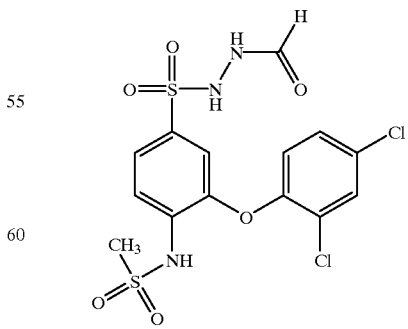

3-(2,4-Dichlorophenoxy)-4-methylsulphonylamino-benzenesulphonic acid chloride (1.1 g, 2.5 mmol) was dissolved in $CH_2Cl_2$ (5 ml) and at 0° C. added dropwise to a solution of formylhydrazine (0.18 g, 3.0 mmol) in pyridine (20 ml). The mixture was stirred for 1 hour at 0° C. and then evaporated down. The residue was dried in vacuo and purified by chromatography (silica gel, chloroform/MeOH 19/1). Yield: 0.73 g=64% $^{13}C$ (100 MHz, DMSO-$d_6$) δ 166.84, 159.45, 150.27, 150.15, 147.20, 146.95, 134.81, 133.25, 130.32, 129.27, 129.07, 125.82, 124.43, 124.19, 124.01, 123.03, 122.89, 122.33, 122.14, 116.68, 116.35, 40.95, 40.88

EXAMPLE 56

3-(3,4-Dichlorophenylthio)-4-methylsulphonylaminobenzenesulphonamide

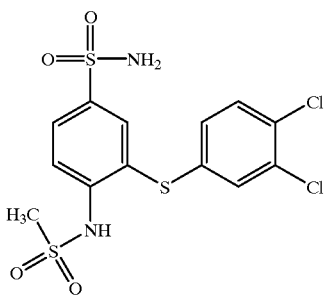

EXAMPLE 57

3-(3,4-Dichlorophenylthio)-4-methylsulphonylaminobenzenesulphonamide

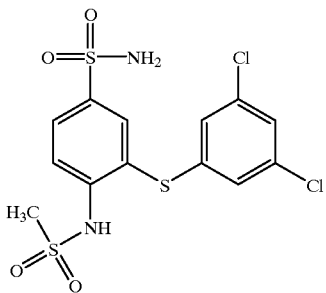

EXAMPLE 58

3-(2,4-Dimethylphenylthio)-4-methylsulphonylaminobenzenesulphonamide

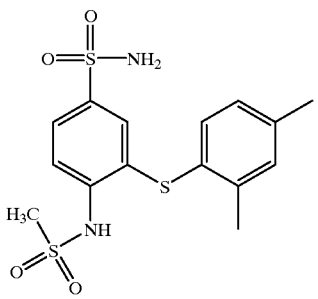

EXAMPLE 59

3-(2-Chloro-4-methylphenylthio)-4-methylsulphonylaminobenzenesulphonamide

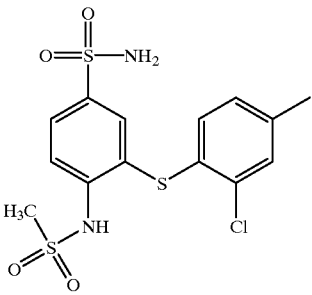

EXAMPLE 60

3-(2-Methyl-4-chlorophenylthio)-4-methylsulphonylaminobenzenesulphonamide

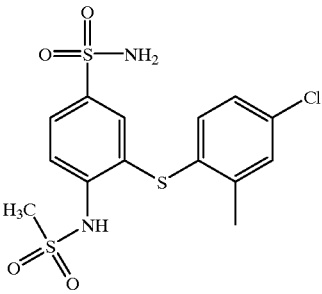

EXAMPLE 61

3-(2-Chloro-4-trifluoromethylphenylthio)-4-methylsulphonylamino-benzenesulphonamide

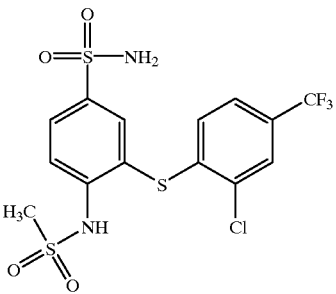

EXAMPLE 62

3-(2,6-Dichlorophenylthio)-4-methylsulphonylaminobenzenesulphonamide

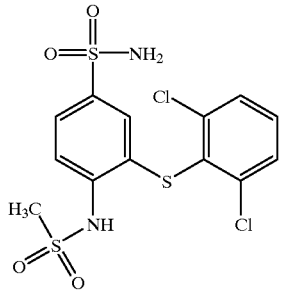

EXAMPLE 63

3-(2,4-Dichlorophenylamino)-4-methylsulphonylaminobenzenesulphonamide

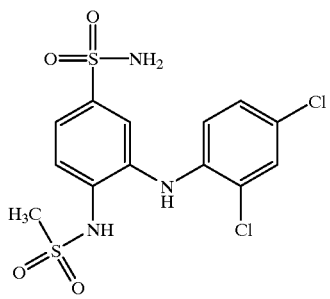

EXAMPLE 64

3-(4-Chlorophenylamino)-4-methylsulphonylaminobenzenesulphonamide

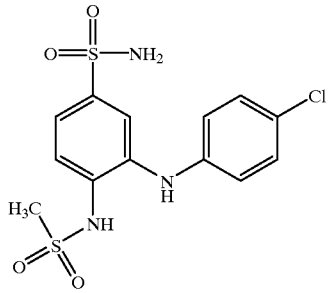

EXAMPLE 65

3-(2,4,6-Trichlorophenylamino)-4-methylsulphonylaminobenzenesulphonamide

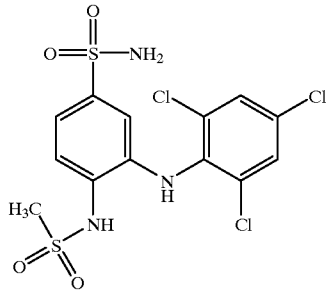

EXAMPLE 66

3-(2-Chlorophenylamino)-4-methylsulphonylaminobenzenesulphonamide

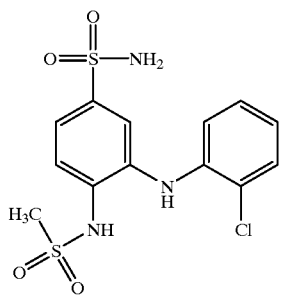

EXAMPLE 67

3-(3-Chlorophenylamino)-4-methylsulphonylaminobenzenesulphonamide

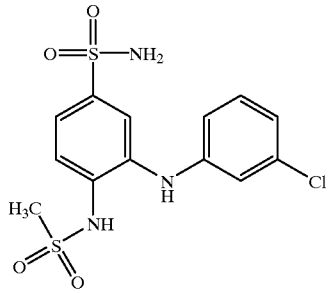

EXAMPLE 68

3-(2,6-Dichlorophenylamino)-4-methyl-sulphonylaminobenzenesulphonamide

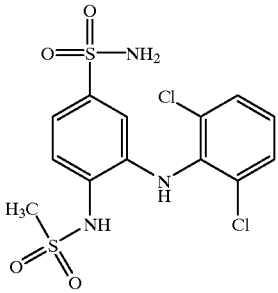

EXAMPLE 69

3-(2-Chloro-4-methoxyphenylamino)-4-methylsulphonylaminobenzenesulphonamide

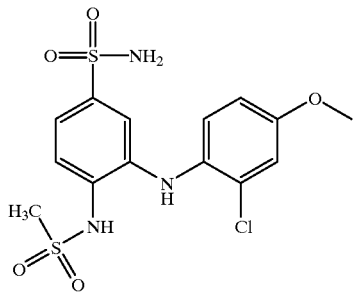

EXAMPLE 70

3-(2-Fluoro-4-chlorophenylamino)-4-methylsulphonylaminobenzenesulphonamide

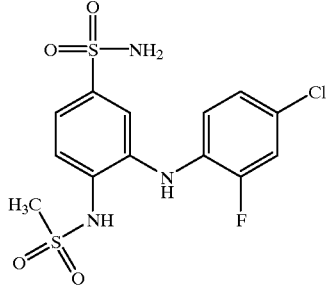

EXAMPLE 71

3-(4-Bromophenylamino)-4-methylsulphonyl-aminobenzenesulphonamide

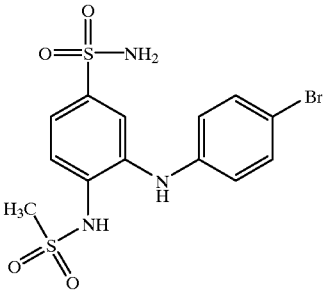

EXAMPLE 72

3-(4-Fluorophenylamino)-4-methylsulphonyl-aminobenzenesulphonamide

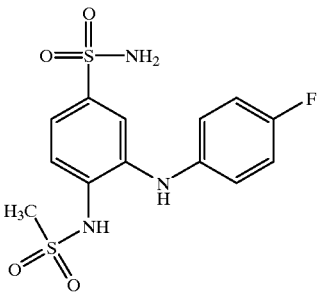

EXAMPLE 73

3-(3-Fluorophenylamino)-4-methylsulphonyl-aminobenzenesulphonamide

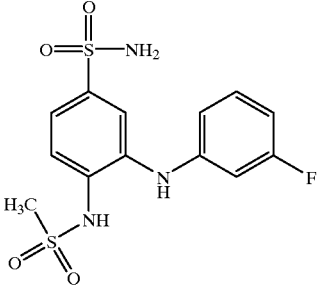

EXAMPLE 74

3-(2-Fluorophenylamino)-4-methylsulphonylaminobenzenesulphonamide

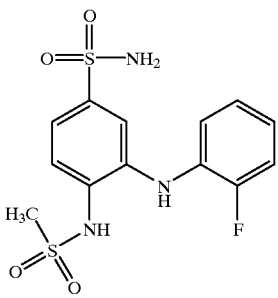

EXAMPLE 75

3-(2,4-Dichlorophenylthio)-4-trifluoromethylsulphonylaminobenzenesulphonamide

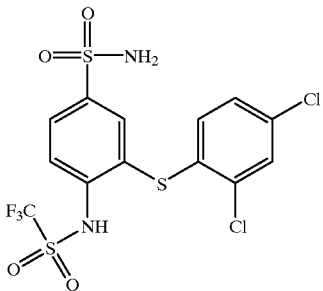

3-(2,4-Dichlorophenylthio)-4-aminobenzenesulphonamide (1.00 g, 2.86 mmol) were dissolved in $CH_2Cl_2$ (50 ml) and triethylamine (4.00 ml, 28.6 mmol) were added. The mixture was cooled to 0° C. and trifluoromethanesulphonyl chloride (2.42 ml, 22.9 mmol) was added dropwise. The reaction solution was stirred for 30 minutes at 0° C. and then for 2 hours at ambient temperature. It was hydrolysed with 1N HCl, extracted with $CH_2Cl_2$ and the combined organic phases were dried over $MgSO_4$. The product was purified by chromatography (silica gel, $CH_2Cl_2$/MeOH 15/1). Yield: 0.15 g=11% $^{13}C$ (100 MHz, $CDCl_3$) δ 151.39, 136.07, 134.56, 133.88, 131.84, 131.62, 130.06, 129.51, 129.31, 127.58, 127.55, 126.20, 122.89, 119.58, 114.70, 111.42

EXAMPLE 76

[3-(2,4-Dichlorophenylthio)-4-trifluoromethylsulphonylaminobenzenesulphonamide] sodium salt

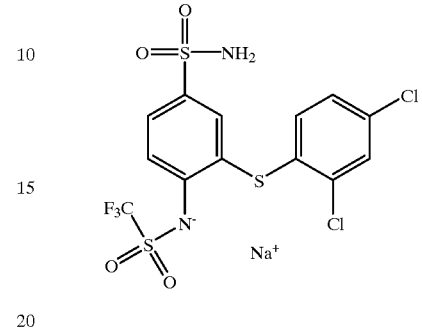

EXAMPLE 77

3-(2,4-Dichlorophenylthio)-4-trichloromethylsulphonylaminobenzenesulphonamide

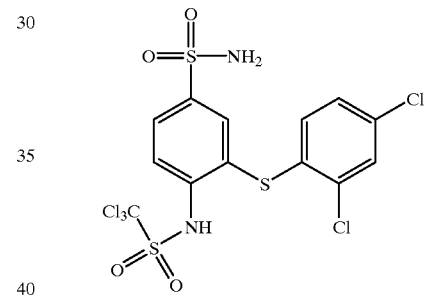

EXAMPLE 78

3-(2,4-Dichlorophenylthio)-4-isopropylsulphonylaminobenzenesulphonamide

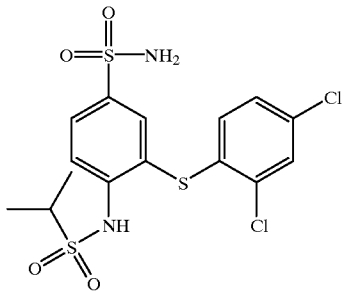

EXAMPLE 79

3-(2,4-Dichlorophenylthio)-4-ethyl-sulphonylaminobenzenesulphonamide

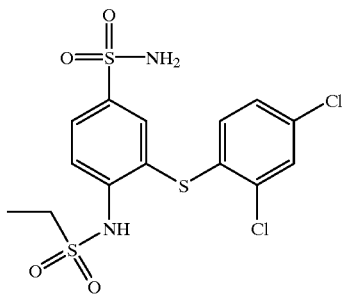

(a) 2-(2,4-Dichlorophenylthio)-N-ethylsulphonylanilide

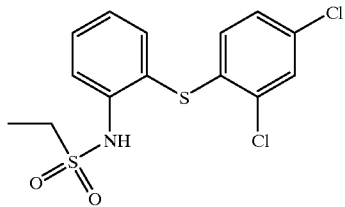

Synthesis was carried out analogously to Example 1(c). The product was purified by chromatography (silica gel, $CH_2Cl_2$). $^{13}C$ (100 MHz, $CDCl_3$)d 139.98, 137.64, 133.48, 132.73, 132.15, 129.77, 128.35, 127.88, 125.18, 118.99, 118.87, 46.73, 8.12

(b) 3-(2,4-Dichlorophenylthio)-4-ethylsulphonylamino-benzenesulphonamide

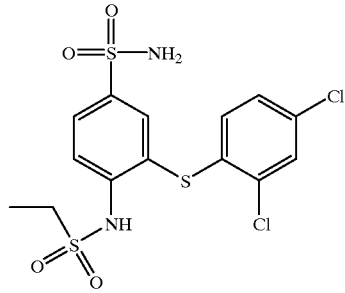

Synthesis was carried out analogously to Examples 1(d) and (e). The product was recrystallised from $CH_2Cl_2$/MeOH. $^{13}C$ (100 MHz, DMSO-$d_6$)d 141.78, 141.11, 134.04, 132.89, 132.81, 132.03, 131.06, 129.71, 128.58, 127.23, 127.12, 125.20, 47.70, 8.11

EXAMPLE 80

3-(2,4-Dichlorophenylthio)-4-propyl-sulphonylaminobenzenesulphonamide

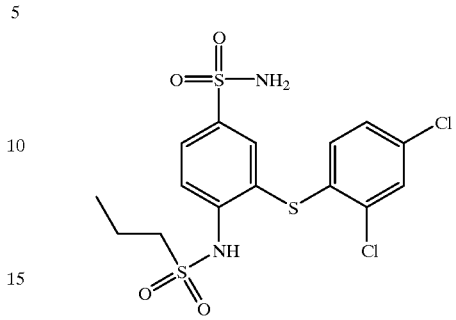

EXAMPLE 81

3-(2,4-Dichlorophenylthio)-4-(2-chloro-ethylsulphonylamino)benzenesulphonamide

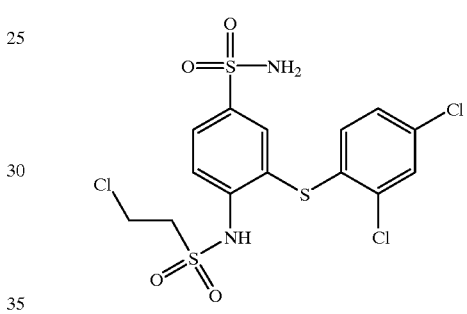

EXAMPLE A

Human COX-2 Test

Cells from a human monocytoid cell line are stimulated with LPS (incubator at 37° C., 5% $CO_2$-enriched atmosphere and approximately 100% relative humidity), in order to induce COX-2. Then the culture medium (RPMI 1640 enriched with 10% FCS, 2 mM glutamine, 10,000 U/ml penicillin, 10 ng/ml.streptomycin and 1 mM pyruvate) was renewed and potential inhibitors of cyclooxygenase-2, dissolved in culture medium or in phosphate-buffered saline or in any other solvent which is compatible with cell culture, were added and incubated for half an hour as described above. Arachidonic acid was pipetted in and incubation was continued for 15 minutes. The culture supernatant of the cells was removed and its content of products of cyclooxygenase metabolism (such as prostaglandin E2, prostaglandin $F_{1\alpha}$ and thromboxane $B_2$) was measured by ELISA.

EXAMPLE B

Human COX 1 test

The inhibition of arachidonic acid-induced aggregation of washed human thrombocytes was used as a test system for assessing the inhibition of cyclooxygenase I. The test substances were added to a thrombocyte suspension at 37° C. 2 minutes before the addition of the arachidonic acid (final concentration 10 μM) and the course of aggregation was measured using an aggregometer. By means of a concentration-activity curve the concentration of test substance at which 50% aggregation is measured was determined ($IC_{50}$).

The results of the two tests and the selectivity obtained from them are shown in Table 1.

TABLE 1

| Compound | COX I IC50 μM | COX II IC50 μM | COX I/COX II |
|---|---|---|---|
| 1 | ≧50 | 0.10 | ≧500 |
| 4 | ≧45 | 0.11 | ≧450 |
| 6 | 52 | 0.2 | 260 |
| 7 | 27 | 0.027 | 1000 |
| 8 | 11 | 0.15 | 73 |
| 17 | 60 | 0.17 | 353 |
| 19 | ≧60 | 0.54 | ≧110 |
| 25 | ≧35 | 0.17 | ≧196 |
| 26 | ≧70 | 0.27 | ≧253 |

We claim:

1. Compounds of formula I

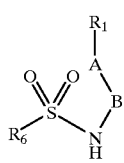

wherein

A denotes oxygen, sulphur or NH, $R_1$ denotes a cycloalkyl, aryl or heteroaryl group optionally mono- or polysubstituted by halogen, alkyl, $CF_3$ or alkoxy B denotes a group of formula IIa or IIb

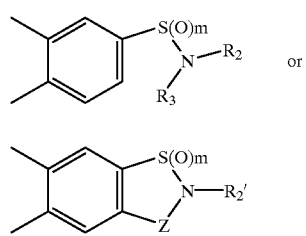

$R_2$ and $R_3$ independently of each other denote hydrogen, an optionally polyfluorinated alkyl radical, an aralkyl, aryl or heteroaryl radical or a radical $(CH_2)_n$—X, or $R_2$ and $R_3$ together with the N-atom denote a three- to seven-membered, saturated, partially or totally unsaturated heterocycle with one or more heteroatoms N, O or S, which may optionally be substituted by oxo, an alkyl, alkylaryl or aryl group or a group $(CH_2)_n$—X, $R_2$' denotes hydrogen, an optionally polyfluorinated alkyl group, an aralkyl, aryl or heteroaryl group or a group $(CH_2)_n$—X, wherein X denotes halogen, $NO_2$, —$OR_4$, —$COR_4$, —$CO_2R_4$, —$OCO_2R_4$, —CN, —$CONR_4OR_5$, —$CONR_4R_5$, —$SR_4$, —$S(O)R_4$, —$S(O)_2R_4$, —$NR_4R_5$, —NHC(O)$R_4$, —NHS(O)$_2R_4$ Z denotes —$CH_2$—, —$CH_2$—$CH_2$—, —$CH_2$—$CH_2$—$CH_2$—, —$CH_2$—CH=CH—, —CH=CH—$CH_2$—, —$CH_2$—CO—, —CO—$CH_2$—, —NHCO—, —CONH—, —NHCH$_2$—, —$CH_2$NH—, —N=CH—, —NHCH—, —$CH_2$—$CH_2$—NH—, —CH=CH—, >N—$R_3$, >C=O, >S(O)$_m$, $R_4$ and $R_5$ independently of each other denote hydrogen, alkyl, aralkyl or aryl, n is an integer from 0 to 6, $R_6$ is a straight-chained or branched $C_{1-4}$-alkyl group which may optionally be mono- or polysubstituted by halogen or alkoxy, or $R_6$ denotes $CF_3$, and m denotes an integer from 0 to 2, with the proviso that A does not represent O if $R_6$ denotes $CF_3$, and the pharmaceutically acceptable salts thereof.

2. Compounds of formula I according to claim 1, wherein $R_1$ denotes a cyclopentyl, cyclohexyl, phenyl, pyridyl, thienyl or thiazolyl group optionally mono- or polysubstituted by halogen, methoxy, methyl or ethyl.

3. Compounds of formula I according to claim 2, wherein $R_1$ denotes a cyclohexyl group, a phenyl group, a 2,4-dichlorophenyl group or a 2,4-difluorophenyl group.

4. Pharmaceutical composition containing as active substance at least one compound of general formula I according to claim 1.

5. A method for the treatment of diseases or disorders which can be cured or alleviated by inhibiting the enzyme cyclooxygenase II, which comprises administering to a patient in need of such treatment, a compound of formula I

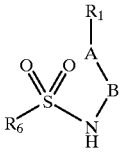

wherein

A denotes oxygen, sulphur or NH, $R_1$ denotes a cycloalkyl, aryl or heteroaryl group optionally mono- or polysubstituted by halogen, alkyl, $CF_3$ or alkoxy B denotes a group of formula Ia or IIb

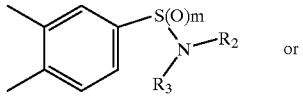

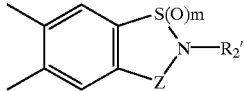

$R_2$ and $R_3$ independently of each other denote hydrogen, an optionally polyfluorinated allyl radical, an aralkyl, aryl or heteroaryl radical or a radical $(CH_2)_n$—X, or $R_2$ and $R_3$ together with the N-atom denote a three- to seven-membered, saturated, partially or totally unsaturated heterocycle with one or more heteroatoms N, O or S, which may optionally be substituted by oxo, an alkyl, alkylaryl or aryl group or a group $(CH_2)_n$—X, $R_2$' denotes hydrogen, an optionally polyfluorinated alkyl group, an aralkyl, aryl or heteroaryl group or a group $(CH_2)_n$—X, wherein X denotes halogen, $NO_2$, $-OR_4$, $-COR_4$, $-CO_2R_4$, $-OCO_2R_4$, $-CN$, $-CONR_4OR_5$, $-CONR_4R_5$, $-SR_4$, $-S(O)R_4$, $-S(O)_2R_4$, $-NR_4R_5$, $-NCH(O)R_4$, $-NHS(O)_2R_4$, Z denotes $-CH_2-$, $-CH_2-CH_2-$, $-CH_2-CH_2-CH_2-$, $-CH_2-CH=CH-$, $-CH=CH-CH_2-$, $-CH_2-CO-$, $-CO-CH_2-$, $-NHCO-$, $-CONH-$, $-NHCH_2-$, $-CH_2NH-$, $-N=CH-$, $-NHCH-$, $-CH_2-CH_2-NH-$, $-CH=CH-$, $>N-R_3$, $>C=O$, $>S(O)_m$, $R_4$ and $R_5$ independently of each other denote hydrogen, alkyl, aralkyl or aryl, n is an integer from 0 to 6, $R_6$ is a straight-chained or branched $C_{1-4}$-alkyl group which may optionally be mono- or polysubstituted by halogen or alkoxy, and m denotes an integer from 0 to 2, with the proviso that A does not represent O if $R_6$ denotes $CF_3$, and the pharmaceutically acceptable salts thereof.

6. The method according to claim 5 which comprises treating inflammatory processes.

7. The method according to claim 5 which comprises treating pain.

* * * * *